(12) United States Patent
Rigatti et al.

(10) Patent No.: US 10,428,363 B2
(45) Date of Patent: *Oct. 1, 2019

(54) AMPLIFICATION METHODS TO MINIMISE SEQUENCE SPECIFIC BIAS

(71) Applicant: Illumina Cambridge Limited, Nr Saffron Walden (GB)

(72) Inventors: Roberto Rigatti, Arco (IT); Jonathan Mark Boutell, Nr Saffron Walden (GB); Min-Jui Richard Shen, Rancho Santa Fe, CA (US)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/295,811

(22) Filed: Oct. 17, 2016

(65) Prior Publication Data

US 2017/0029857 A1 Feb. 2, 2017

Related U.S. Application Data

(63) Continuation of application No. 14/299,269, filed on Jun. 9, 2014, now Pat. No. 9,469,872, which is a continuation of application No. 13/580,336, filed as application No. PCT/US2011/025851 on Feb. 23, 2011, now Pat. No. 8,759,037.

(60) Provisional application No. 61/362,415, filed on Jul. 8, 2010, provisional application No. 61/327,010, filed on Apr. 22, 2010, provisional application No. 61/307,277, filed on Feb. 23, 2010.

(51) Int. Cl.
*C12P 19/34* (2006.01)
*C12Q 1/686* (2018.01)
*C09K 3/00* (2006.01)

(52) U.S. Cl.
CPC ............... *C12P 19/34* (2013.01); *C09K 3/00* (2013.01); *C12Q 1/686* (2013.01)

(58) Field of Classification Search
CPC ............. C12Q 1/686; C12Q 2527/137; C12Q 2565/518; C09K 3/00; C12P 19/34
USPC ......................................................... 435/91.2
See application file for complete search history.

(56) References Cited

U.S. PATENT DOCUMENTS

| 5,302,509 | A | 4/1994 | Cheeseman |
| 6,664,079 | B2 | 12/2003 | Ju et al. |
| 7,057,026 | B2 | 6/2006 | Barnes et al. |
| 7,541,444 | B2 | 6/2009 | Milton et al. |
| 7,544,794 | B1 | 6/2009 | Benner |
| 8,759,037 | B2 | 6/2014 | Rigatti |
| 2008/0199916 | A1* | 8/2008 | Zheng .................. C12Q 1/6844 435/91.2 |
| 2009/0088327 | A1 | 4/2009 | Rigatti et al. |
| 2009/0118128 | A1 | 5/2009 | Liu et al. |
| 2010/0009871 | A1 | 1/2010 | Reed et al. |

FOREIGN PATENT DOCUMENTS

| EP | 1 591 541 A3 | 7/2006 |
| WO | 2004/018497 A2 | 3/2004 |
| WO | 2005/065814 A1 | 7/2005 |
| WO | 2009/098298 A1 | 8/2009 |
| WO | 2009/099602 A1 | 8/2009 |
| WO | 2010/093552 A1 | 8/2010 |

OTHER PUBLICATIONS

Korch, C., DNA sequencing Services and Sample Preparation Guidelines., CU-Cancer Center DNA sequencing & Analysis Core, University of Colorado Denver—School of Medicine, http://DNAsequencingCore.ucdenver.edu, pp. 1-15, April (Year: 2010).*
Polz et al., Applied Environ. Microbiol., 64(10):3724-3725 (Year: 1998).*
Henke et al., Nucleic Acid Research., 25(19): 3957-3958 (Year: 1997).*
Baskaran, et al., Genome Research, vol. 6, 1996, 633-638.
Bentley, et al., "Accurate whole human genome sequencing using reversible terminator chemistry", Nature, vol. 456, Nov. 6, 2008, 53-59.
Elnifro, E.M. et al., "Multiplex PCR: optimization and application in diagnostic virology", Clinical Microbiology Reviews, vol. 13(4), Oct. 2000, 559-570.
European Search Report, "Application No. 11747961.8".
Henke, et al., "Betaine improves the PCR amplification of GC-rich DNA sequences", Nucleic Acids Research, vol. 25, No. 19, Jan. 1, 1997, 3957-3958.
Hosono, et al., "Unbiased whole-genome amplification directly from clinical samples", Genome Research, 13(5), 2003, 954-964.
Kunz, et al., "Modulation of Mutagenesis by Deoxyribonucleotide Levels", Annu. Rev. Genet. 25, 1991, 339-59.

(Continued)

*Primary Examiner* — Cynthia B Wilder
(74) *Attorney, Agent, or Firm* — Illumina, Inc.

(57) ABSTRACT

Methods for amplifying nucleic acids are provided. The methods can be used to minimize sequence specific bias caused by the preferential amplification of certain nucleic acid sequences. Methods are described which can lower the efficiency of AT rich templates relative to GC rich templates, thereby minimizing GC bias during amplification reactions with multiple templates of different sequence. The methods are suited to solid phase amplification, for example, utilizing flow cells.

19 Claims, 5 Drawing Sheets

Specification includes a Sequence Listing.

(56) References Cited

OTHER PUBLICATIONS

Markoulatos, P. et al., "Multiplex polymerase chain reaction: a practical approach", Journal of Clinical Laboratory Analysis, vol. 16(1), 2002, 47-51.

Polz, M.F. et al., "Bias in Template-to-Product Ratios in Multitemplate PCR", Applied and Environmental Microbiology. vol. 64(10), Oct. 1, 1998, 3724-3730.

Wojdacz, T.K. et al., "Primer design versus PCR bias in methylation independent PCR amplifications", Epigenetics. vol. 4(4), May 14, 2009, 231-234.

Fromant, M. "Direct Random Mutagenesis of Gene-Sized DNA Fragments Using Polymerase Chain Reaction", Analytical Biochemistry, vol. 224, 1995, 347-353.

Mamedov, T. et al., "A fundamental study of the PCT amplification of GC-rich DNA templates", Computational Biology and Chemistry, vol. 32, 2008, 452-457.

Mutter, G. et al., "PCR bias in amplification of androgen receptor alleles, a trinucleotide repeat marker used in clonality studies", Nucleic Acids Research, vol. 23, No. 8, 1995, 1411-1418.

\* cited by examiner

AMPLIFICATION METHODS TO MINIMISE SEQUENCE SPECIFIC BIAS

CROSS REFERENCE TO RELATED APPLICATIONS

The present application is a continuation of U.S. application Ser. No. 14/299,269, filed Jun. 9, 2014, now U.S. Pat. No. 9,469,872, which is a continuation of U.S. application Ser. No. 13/580,336, now U.S. Pat. No. 8,759,037, which is a U.S. National Phase Application of PCT/US2011/025851, filed on Feb. 23, 2011, which claims priority to U.S. Ser. No. 61/307,277, filed Feb. 23, 2010; U.S. Ser. No. 61/327,010, filed Apr. 22, 2010; and U.S. Ser. No. 61/362,415, filed Jul. 8, 2010. Each of these applications is incorporated by reference herein in its entirety.

FIELD OF THE INVENTION

The invention relates to methods of amplification of polynucleotide sequences and in particular relates to methods for amplification of polynucleotide sequences to minimise sequence specific biases. The methods according to the present invention are suited to solid phase amplification, for example, utilising flow cells.

BACKGROUND TO THE INVENTION

Several publications and patent documents are referenced in this application in order to more fully describe the state of the art to which this invention pertains. The disclosure of each of these publications and documents is incorporated by reference herein.

The Polymerase Chain Reaction or PCR (Saiki et al 1985, Science 230:1350) has become a standard molecular biology technique which allows for amplification of nucleic acid molecules. This in-vitro method is a powerful tool both for the detection and analysis of small quantities of nucleic acids and other recombinant nucleic acid technologies.

Briefly, PCR typically utilizes a number of components: a target nucleic acid molecule, a molar excess of a forward and reverse primer which bind to the target nucleic acid molecule, deoxyribonucleoside triphosphates (dATP, dTTP, dCTP and dGTP) and a polymerase enzyme.

The PCR reaction is a DNA synthesis reaction that depends on the extension of the forward and reverse primers annealed to opposite strands of a dsDNA template that has been denatured (melted apart) at high temperature (90° C. to 100° C.) Using repeated melting, annealing and extension steps usually carried out at differing temperatures, copies of the original template DNA are generated.

Amplification of template sequences by PCR typically draws on knowledge of the template sequence to be amplified such that primers can be specifically annealed to the template. The use of multiple different primer pairs to simultaneously amplify different regions of the sample is known as multiplex PCR, and suffers from numerous limitations, including high levels of primer dimerisation, and the loss of sample representation due to the different amplification efficiencies of the different regions.

For the multiplex analysis of large numbers of target fragments, it is often desirable to perform a simultaneous amplification reaction for all the targets in the mixture, using a single pair of primers for all the targets. In certain embodiments, one or more of the primers may be immobilised on a solid support. Such universal amplification reactions are described more fully in application US2005/0100900 (Method of Nucleic Acid Amplification), the contents of which are incorporated herein by reference in their entirety. Isothermal amplification methods for nucleic acid amplification are described in US2008/0009420, the contents of which are incorporated herein by reference in their entirety. The methods involved may rely on the attachment of universal adapter regions, which allows amplification of all nucleic acid templates from a single pair of primers. However the universal amplification reaction can still suffer from limitations in amplification efficiency related to the sequences of the templates. One manifestation of this limitation is that the mass or size of different nucleic acid clusters varies in a sequence dependent manner. For example, the AT rich clusters can gain more mass or become larger than the GC rich clusters. As a result, analysis of different clusters may lead to bias. For example, in applications where clusters are analyzed using sequencing by synthesis techniques the GC rich clusters may appear smaller or more dim such that the clusters are detected less efficiently. This results in lower representation of sequence data for GC rich clusters than the brighter (more intense) and larger AT rich clusters. This can result in lower representation and less accurate sequence determination for the GC rich templates, an effect which may be termed GC bias. The presence of sequence specific bias during amplification gives rise to difficulties determining the sequence of certain regions of the genome, for example GC rich regions such as CpG islands in promoter regions. The resulting lack of sequence representation in the data from clusters of different GC composition translates into data analysis problems such as increases in the number of gaps in the analyzed sequence; a yield of shorter contigs, giving rise to a lower quality de novo assembly; and a need for increased coverage to sequence a genome, thereby increasing the cost of sequencing genomes.

In particular embodiments, the methods and compositions presented herein are aimed at limiting the sequence specific biases found in nucleic acid amplification reactions. In certain embodiments, the methods of amplification normalise the intensity of nucleic acid clusters of different sequences, and minimise the population size variance between amplified nucleic acid species having different sequences. The problem of bias may be more acute when the density of clusters on the solid support is high. In certain situations, as the clusters grow, the amplification primers on the solid support are all extended, and hence adjacent clusters can not expand over the top of each other due to the lack of available amplification primers. The over-amplification of AT rich sequences causes rapid consumption of the primers on the surface, and hence reduces the ability of the GC rich sequences to amplify. The amplification methods described herein are therefore particularly useful in order to obtain a high cluster density on a solid support where different clusters contain AT and GC rich sequences.

SUMMARY OF THE INVENTION

Methods and compositions for normalising the amplification of nucleic acid templates of different sequence are provided. Certain methods and compositions involve decreasing the efficiency with which AT rich sequences are amplified and/or increasing the efficiency with which GC rich sequences are amplified.

The methods may include amplifying different nucleic acid templates under conditions wherein a subset of nucleotide types are incorporated into copies of the templates at a lower efficiency compared to at least one other type of nucleotide, thereby producing a plurality of different copies, wherein the amplifying comprises at least two cycles whereby the plurality of different copies are used as templates in at least a second cycle. In this and other embodiments set forth herein, the nucleic acids form an ensemble and the ensemble can be manipulated using one or more of the techniques or steps set forth herein.

The amplification method may use pools of nucleotides where different nucleotide types are not all present at the same concentration (for example less A and/or T; or more G and/or C). The method may, alternatively, or additionally, use nucleotides which are incorporated less efficiently than the standard nucleotides, for example, dATP or dTTP analogues which incorporate less efficiently than dATP or dTTP. Conversely it is possible to use analogues of G and C which improve the efficiency of incorporation of G and C nucleotides. Alternatively or additionally it is possible to use analogues of A and/or T which raise the stability of the A:T base pairs. In nucleic acid duplexes, G:C base pairs are stronger than A:T base pairs, and thus duplexes rich in A and T bases denature more easily than those rich in G and C bases. Using analogues of A and T which make the A:T base pairing stronger thus increase the strength of the duplex, slowing the denaturation, and lowering the efficiency of the amplification of those A:T rich strands.

Alternatively or additionally, the methods may include amplifying different nucleic acid templates under conditions wherein a subset of nucleotide types are incorporated into copies of the templates at a lower efficiency compared to at least one other type of nucleotide, thereby producing a plurality of different copies, wherein the amplifying is carried out in the presence of additives and comprises at least two cycles whereby the plurality of different copies are used as templates in at least a second cycle.

Also provided is a method for amplifying nucleic acid templates of different sequence comprising a first round comprising one or more cycles of amplification, wherein the cycles of amplification comprise amplifying the nucleic acid templates under conditions favouring AT rich templates; and a second round comprising one or more cycles of amplification, wherein the cycles of amplification comprise amplifying the nucleic acid templates under conditions favouring GC rich templates.

According to another aspect of the invention, also provided is a composition of nucleic acids on a solid support and a solution of at least four different nucleotide triphosphate types wherein the at least four different nucleotide triphosphate types are present at different concentrations in the solution. For example the concentration of dATP and dTTP may be less than half the concentration of dGTP and dCTP.

Further provided herein is an array of nucleic acid clusters of different sequence where each of the clusters is of similar size or mass. The array may comprise a high feature density of clusters per unit area of the solid support, for example greater than 200,000 clusters per mm$^2$, greater than 300,000 clusters per mm$^2$, greater than 400,000 clusters per mm$^2$, greater than 500,000 clusters per mm$^2$, greater than 600,000 clusters per mm$^2$, greater than 700,000 clusters per mm$^2$, greater than 800,000 clusters per mm$^2$, greater than 900,000 clusters per mm$^2$, greater than 1,000,000 clusters per mm$^2$, or higher.

The first flow cell shows that the AT rich (GC poor) monotemplates grow larger and showed more stained intensity than the GC rich clusters. In the second flowcell, the clusters in each of the 8 lanes is of similar brightness and intensity, showing that the amplification of the AT rich clusters has been inhibited by lowering the concentrations of the dATP and dTTP.

Figure 2:
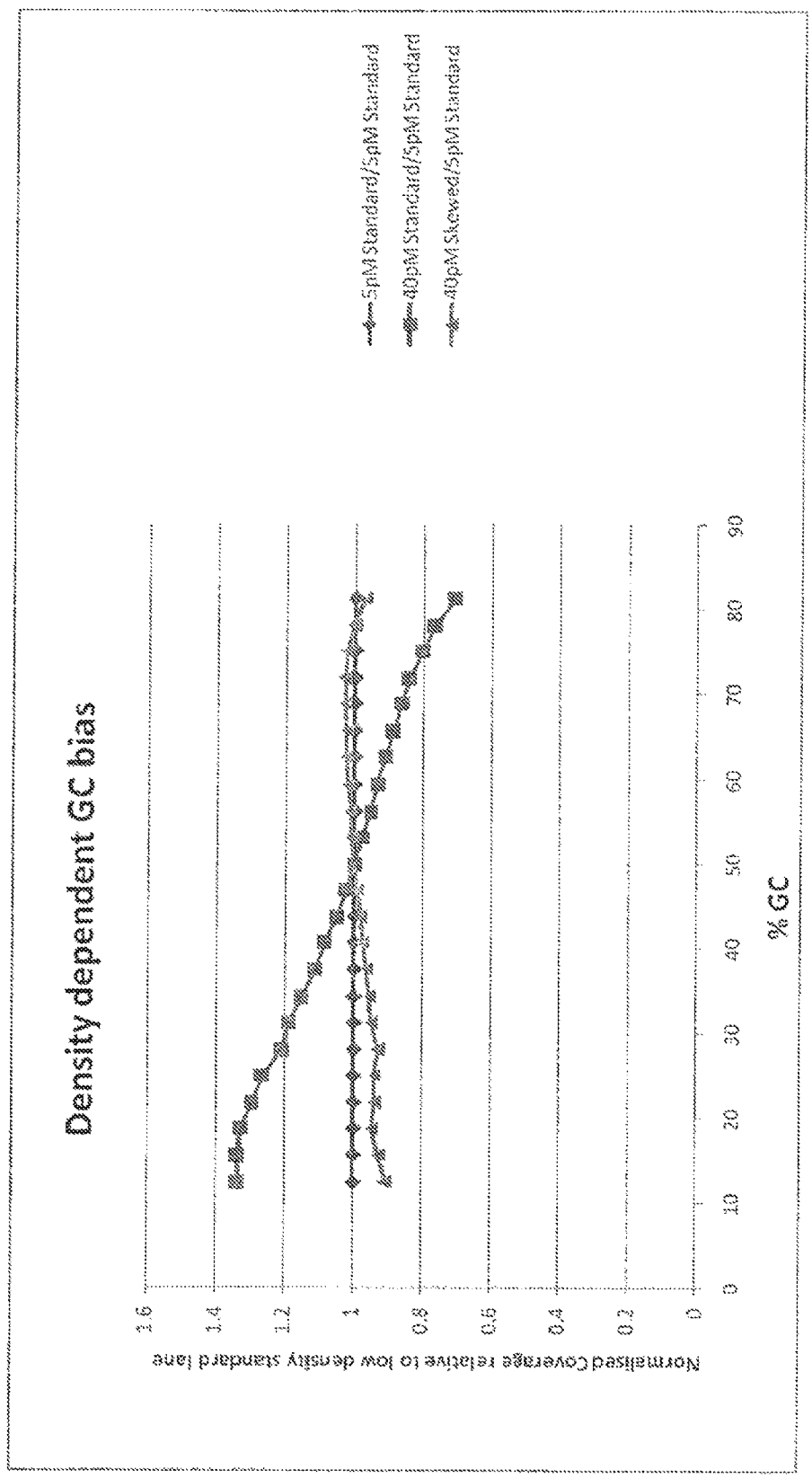

FIG. 2 shows the effect of cluster density on the GC bias. At low template seeding concentration (5 µM) of fragmented E. coli DNA, there is little difference in sequence coverage between GC rich and GC poor regions of the genome as compared to higher concentrations of template DNA. At higher template concentrations (40 µM), where the number of clusters on the surface is higher, the coverage of the GC rich regions of the genome starts to decrease. Amplification using varying dNTP concentrations (so called 'skewed' nucleotides) using the same 40 µM template concentration, reduces the degree of GC bias to the same as the lower template concentration where GC bias was less apparent. Thus the amplification methods described herein are particularly beneficial when using a high density of cluster amplicons on a solid support.

Figure 3:
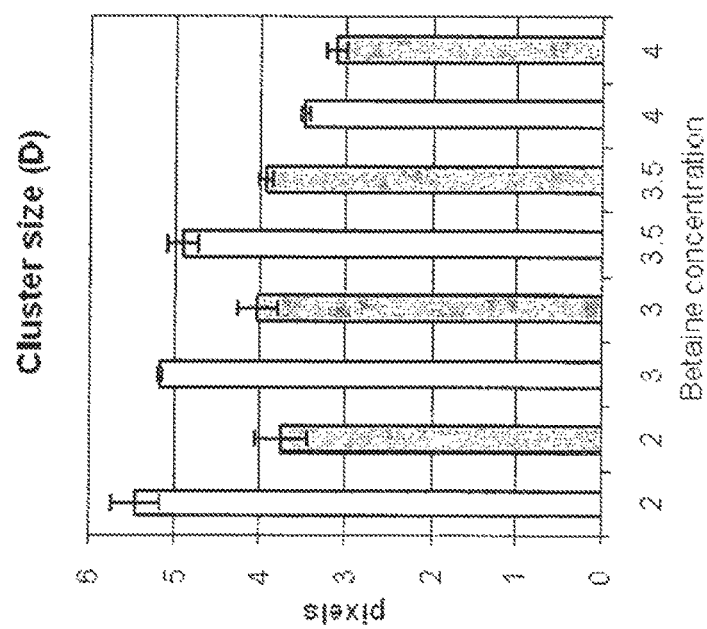

FIG. 3 shows the effect of betaine on cluster intensity. Concentrations of betaine above 2 M lower the size of the clusters in a sequence dependent manner such that the AT rich clusters become proportionally smaller than the GC rich clusters, resulting in GC rich clusters and AT rich clusters of similar size. The lighter bars, corresponding to the AT rich templates, show a more substantial decrease than the darker bars, corresponding to the GC rich templates.

Figure 4:
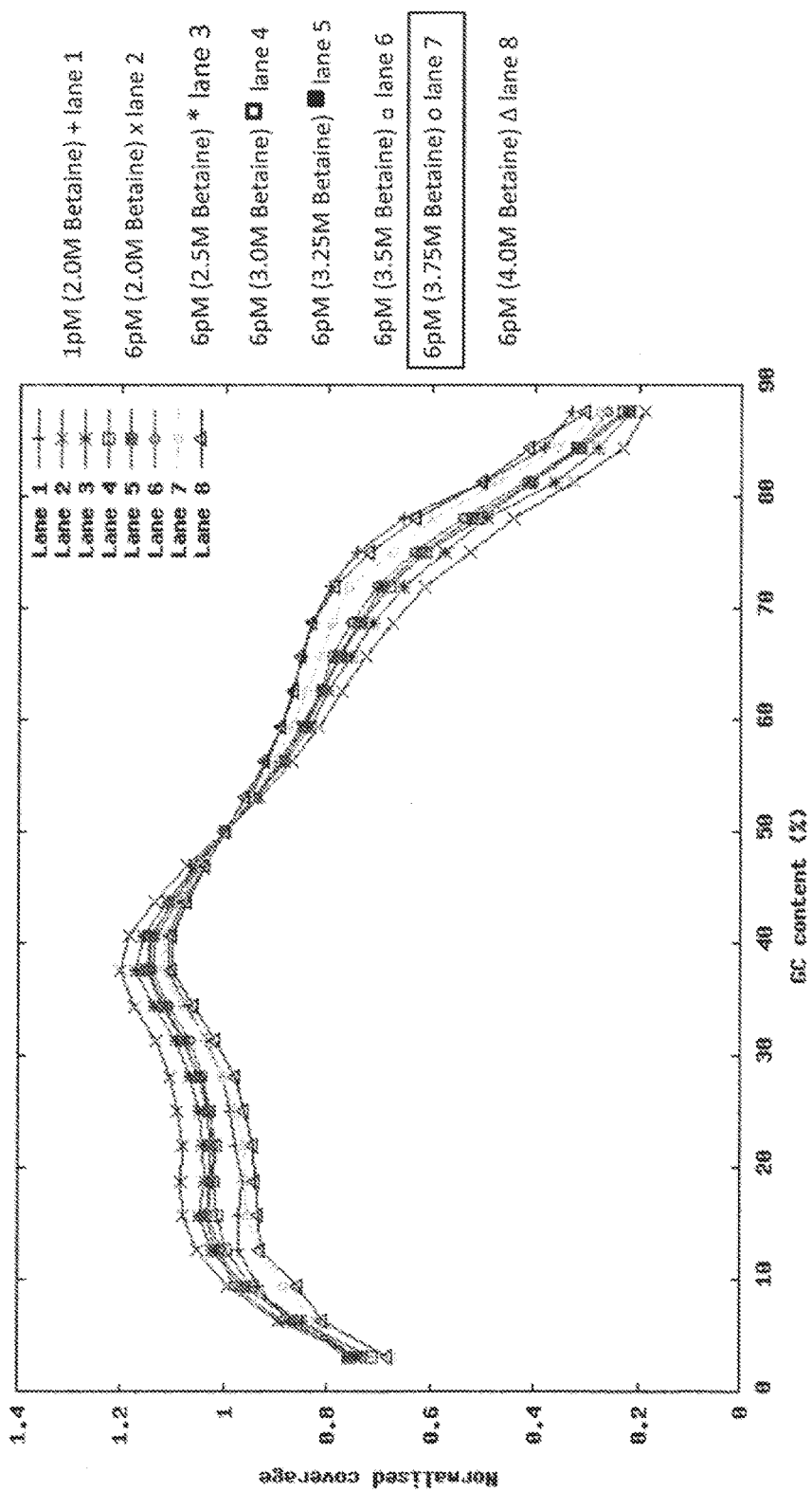

FIG. 4 shows the GC bias versus betaine concentrations of between 2 and 4 M. Higher concentrations of betaine result in less GC bias than lower concentrations of betaine.

Figure 5:
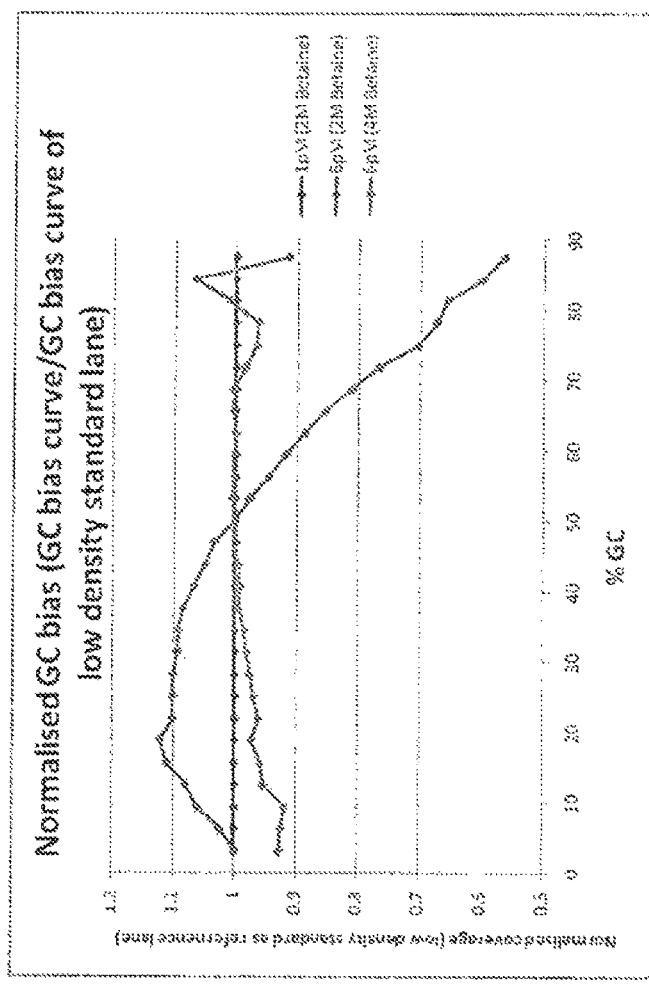

FIG. 5 is a normalised GC bias plot showing that betaine at 4M concentration gives less GC bias than betaine at 2 M concentration.

DETAILED DESCRIPTION OF THE INVENTION

In particular embodiments, the invention relates to methods and compositions for normalising the amplification efficiency of different template sequences. One embodiment is a method to normalise the amplification of nucleic acid templates of different sequence by decreasing the efficiency with which AT rich sequences are amplified and/or increasing the efficiency with which GC rich sequences are amplified.

The term "normalise," when used in reference to the amplification of nucleic acid templates, means to alter the ratio of molecules of different type obtained during an amplification process such that the number of molecules of a particular type in the population is made more equal to the number of molecules of another type in the population. Thus for an amplification reaction carried out on a population of nucleic acid templates of different sequence, to normalise the amplification can mean lowering any sequence specific biases which would otherwise result in certain members of the population increasing in number more than other members of the population. The normalisation process can be used to produce relative ratios of the fragments in the population that are the same after the amplification as they were in the population before amplification. Thus for example a population comprising 1 million molecules of different sequence will contain, after amplification, on average the same number of copies of each of the 1 million fragments without any specific biases for certain sequences. It will be understood that this is a statistical measure and that the absence of bias can be within an acceptable variance such as within 0.5, 1, 2, 3, 4, 5, 10, 15, 20, 25, 30, 35, 40, 45 or 50% variance in the number of copies for each fragment. When carried out on a solid support to make nucleic acid clusters, the normalisation of the amplification results in an array of clusters with a similar number of molecules in each cluster, and thus similar sizes and signal intensities.

The term "different" when used in reference to two or more nucleic acids means that the two or more nucleic acids have nucleotide sequences that are not the same. For example, two nucleic acids can differ due to one sequence being longer than the other and conversely one sequence being shorter than the other. Two nucleic acids can differ in the content and order of nucleotides in the sequence of one nucleic acid compared to the other nucleic acid, independent of any differences in sequence length between the two nucleic acids. The term can be used to describe nucleic acids whether they are referred to as copies, amplicons, templates, targets, primers, oligonucleotides, polynucleotides or the like.

As described herein, nucleic acid templates containing a high level of A and T bases typically amplify more efficiently than nucleic acid templates with a high level of G and C bases. Nucleic acid templates with sequences containing a high level of A or T bases compared to the level of G or C bases are referred to throughout as AT rich templates or templates with high AT content. Accordingly, AT rich templates can have relatively high levels of A bases, T bases or both. A and T bases. Similarly, nucleic acid templates with sequences containing a high level of G or C bases compared to the level of A or T bases are referred to throughout as GC rich templates or templates with high GC content. Accordingly, GC rich templates can have relatively high levels of G bases, C bases or both G and C bases. The terms GC rich and high GC content are used interchangeably. Similarly, the terms AT rich and high AT content are used interchangeably. The phrases GC rich and AT rich, as used herein, refer to a nucleic acid sequence having a relatively high number of G and/or C bases or A and/or T bases, respectively, in its sequence, or in a part or region of its sequence, relative to the sequence content contained within a control. In this case, the control can be similar nucleic acid sequences, genes, or the genomes from which the nucleic acid sequences originate. Generally, nucleic acid sequences having greater than about 52% GC or AT content are considered GC rich or AT rich sequences. Optionally, the GC content or AT content is greater than 55, 60, 65, 70, 75, 80, 85, 90, 95 or 99%. Nucleic acid sequences containing discrete regions of high GC to AT content may also be considered GC rich or AT rich, respectively. The methods provided herein normalise the efficiencies or levels of amplification of templates with different sequence, for example, with high AT and/or GC content.

In some embodiments, nucleic acids are provided in an ensemble. As used herein, the term "ensemble," when used in reference to nucleic acid molecules, means a collection of nucleic acid molecules that are together. For example, the nucleic acid molecules can be together in a common vessel (e.g., tube, flow cell, well of a microtiter plate, and the like), the nucleic acids can be in fluid communication with each other or with a component of the fluid, the nucleic acids can be on a surface that is contacted with a common fluid or the nucleic acids can be attached to beads in a slurry or emulsion. An ensemble can include nucleic acid molecules having different sequences. Alternatively or additionally, an ensemble can include many nucleic acids having the same sequence. Thus, an ensemble can include many different nucleotide sequences one or more of which are present in two or more copies, or an ensemble can be homogeneous with respect to having only a single nucleotide sequence present. In particular embodiments, nucleic acid templates in an ensemble are substantially the same length and/or copies produced from the templates are substantially the same length.

The methods and compositions set forth herein are particularly useful for making and using nucleic acid clusters on solid supports. Amplification methods that reduce the efficiency of amplification of AT rich sequences can result in clusters having a smaller size or reduced mass. Similarly, amplification methods that increase the efficiency of amplification of GC rich sequences results in clusters of a greater size or greater mass. Accordingly, when detected, for example, using optical means, the AT rich clusters that are made in this way will appear to have a lower intensity and the GC rich clusters will appear to have a higher intensity. The lowering of the intensity is related to the level of AT sequence, thus the AT rich clusters are inhibited more than the GC rich clusters. However it is subsequently possible to improve the brightness of all clusters, for example, by carrying out a higher number of amplification cycles. Without normalising the level of amplification before trying to increase the brightness of all the clusters, the over-amplified AT rich sequences are still much brighter than the GC rich sequences, and indeed become even more 'over amplified' than the GC rich clusters.

In emulsion PCR, which isolates individual nucleic acid molecules to be amplified with primer-coated beads in aqueous droplets within an oil phase, nucleic acid molecules are amplified coating each bead with clonal copies of a nucleic acid molecule followed by immobilization for later analysis. When detected, for example, using optical means, beads with AT rich sequences will appear to have a lower intensity and beads with GC rich sequences will appear to have a higher intensity. Thus, the brightness of all beads is improved using the methods provided herein, for example, by normalising the level of amplification of nucleic acid molecules of different sequence. Without normalising the level of amplification, the beads with AT rich sequences are much brighter than beads with GC rich sequences.

Methods according to the invention may be carried out by amplifying different nucleic acid templates under conditions wherein a subset of nucleotide types are incorporated into copies of the templates at a lower efficiency compared to at least one other type of nucleotide. The amplification process may entail one or more further cycles of amplification to produce a plurality of different copies whereby the plurality of different copies from previous cycles are used as templates in further cycles. Thus the copies produced in a first amplification cycle may be templates in a second amplification cycle.

In some embodiments, as set forth in further detail below, a lower efficiency of nucleotide incorporation can be obtained by the partial use of terminator moieties. In examples where the lower efficiency of nucleotide incorporation is obtained by the partial use of terminator moieties, a subset of the amplified strands may be terminated by the incorporated nucleotide, and thus unable to be used as templates in further cycles. The subset of non-terminated strands is able to function as templates in further amplification cycles.

Lower efficiency nucleotide incorporation can be due to the level of or rate of nucleotide incorporation being lower for some of the nucleotide types than for other types of nucleotides. This lower efficiency of incorporation results in some sequences being copied less efficiently than other sequences. The amplification of sequences which contain a high level of the bases which are adjusted to incorporate with a lower efficiency will be suppressed during the amplification process. The rate of suppression of different template sequences is proportional to the content of the less efficiently incorporated nucleotide types in the template.

Efficiency of a nucleotide polymerase reaction can be measured in terms of the rate of catalysis ($K_{cat}$) $K_{cat}$ is also called turnover number and denotes the maximum number of enzymatic reactions catalyzed per second. Any method which slows down the rate of catalysis of a nucleic acid polymerase may be useful in reducing sequence specific bias. Methods of slowing down the rate of catalysis may include reducing the effective concentration of nucleotides for incorporation, replacing one nucleotide type with another type which serves as a poorer substrate for the polymerase, for example has a lower binding affinity ($K_d$), or using a nucleotide triphosphate analogue which dissociates more slowly from the polymerase following incorporation. It is also possible to use terminator analogues to inhibit the growth of certain strands. Nucleotide analogues which bind to the polymerase but are not incorporated may also be used. Non limiting examples of particular nucleoside modifications are described further below.

The efficiency of a polymerase reaction can be altered by changing the relative concentrations of the different types of nucleotide triphosphates used in an amplification reaction. Conventional wisdom is that all four nucleotides should be used at the same concentration, as an imbalance in the proportion of the four dNTPs can result in misincorporation into the newly formed DNA strand and contribute to a decrease in the fidelity of DNA polymerase (refs Kunz B A, Kohaimi S E (1991). *Annu. Rev. Genet,* 25: 339-59; PCR: A Practical Approach; Oxford University Press 1991). It is particularly surprising that a nucleotide pool imbalance is helpful in solving the problem of sequencing specific biases in nucleotide amplification, but that the pool imbalance does not result in an increase or in an unacceptable increase in the error rates seen during sequencing, for example, for whole genome sequencing of a plurality of nucleic acid templates of different sequence. If the polymerase was having fidelity problems during amplification, an increase in the error rates of the resultant amplicons would be expected. However, sequence data from clusters obtained using eguimolar nucleotide ratios when compared to data from clusters obtained using skewed nucleotide ratios does not show a measurable difference or may show a measurable but acceptable difference in error rates when the data is aligned against the reference sequence. These results demonstrated that the polymerase fidelity is maintained despite the nucleotide pool imbalance.

Particular embodiments set forth herein are based on the discovery that, when carrying out a solid support bridge amplification process to make clusters, the templates which are made of a high level of A and T bases amplify more efficiently than templates which are made of a high level of G and C bases. It is therefore advantageous to lower the level of AT amplification in order to normalise the level of amplification of templates of different sequence.

By way of example, this can be achieved by using a pool imbalance, or 'skewed ratio' of the nucleotide types used in the amplification process. The nucleotides used in the amplification process may be ribo- or deoxyribonucleotides. The nucleotides used in the amplification may be nucleotide 5' polyphosphates, for example 5' triphosphates. The nucleotides used in the amplification reaction may be the four nucleotide triphosphates typically found in native DNA: dATP, dGTP, dCTP and dTTP. The AT rich clusters are less efficiently amplified if the concentration of either or both of the A and T nucleotides is lower than the concentration of either or both of the G and C nucleotides. For example, the concentration of the A nucleotide may be lower than the individual concentration of each of the other three nucleotides, the concentration of the T nucleotide may be lower than the individual concentration of each of the other three nucleotides, or the concentration of the A and T nucleotides taken together may be lower than the combined concentration of the G and C nucleotides. The imbalance may be obtained by lowering the level of A and/or T nucleotides compared to their typical levels in an amplification reaction, or raising the level of G and/or C nucleotides compared to their typical levels in an amplification reaction. Thus the amplification process may be carried out using one or more cycles of amplification where one or more of the amplification cycles uses four different types of nucleotides which are all present but not at the same concentrations as each other.

In specific examples of conditions described above, the nucleotides may be dATP, dGTP, dCTP and dTTP, which may be present at imbalanced, or skewed concentrations. The concentration of dATP may be less than the individual concentration of dTTP, dCTP or dGTP. The concentration of dTTP may be less than the individual concentration of dATP, dCTP or dGTP. The combined concentration of dTTP and dATP may be lower than the combined concentration of dCTP and dGTP.

Any of a variety of nucleotides or nucleotide analogues can be present in an amplification reaction having imbalanced or skewed concentrations. The concentration of dATP may be less than half of the individual concentration of any other nucleotide in an amplification reaction. The concentration of dTTP may be less than half of the individual concentration of any other nucleotide in an amplification reaction. The combined concentration of dATP and dTTP may be less than half of the combined concentration of any other two nucleotides in an amplification reaction. The concentration of dATP may be less than one quarter of the individual concentration of any other nucleotide in an amplification reaction. The concentration of dTTP may be less than one quarter of the individual concentration of any other nucleotide in an amplification reaction. The combined concentration of dATP and dTTP may be less than one quarter of the combined concentration of any other two nucleotides in an amplification reaction. The concentration of dATP may be less than one tenth of the individual concentration of any other nucleotide in an amplification reaction. The concentration of dTTP may be less than one tenth of the individual concentration of any other nucleotide in an amplification reaction. The combined concentration of dATP and dTTP may be less than one tenth of the concentration of any other two nucleotides in an amplification reaction. The ratio of the nucleotides in an amplification reaction may be even lower than those exemplified above, for example one twentieth, one thirtieth, one fiftieth or one hundredth.

Particular methods of the invention may be carried out wherein the concentration of dATP is less than 20 micromolar, less than 10 micromolar, less than 2 micromolar or lower. Particular methods of the invention may be carried out wherein the concentration of dTTP is less than 20 micromolar, less than 10 micromolar, less than 2 micromolar or lower. Alternatively or additionally, the individual concentrations of dGTP or dCTP in a method of the invention can be 100 micromolar, 200 micromolar, 300 micromolar or higher.

Methods of the invention may be carried out using nucleoside analogues that are less efficiently incorporated by a polymerase. Less efficiently in this context means that the modified nucleotides possess a lower rate of catalysis than the equivalent unmodified nucleotide. Thus for example a modified nucleotide for use in the invention may be a T analogue (such as 2-thio thymidine triphosphate or 5-(2'-deoxy-☐-D-ribofuranosyl)-3-methyl-2-pyridone-5'-triphosphate) which shows a lower efficiency of incorporation than the non-modified thymidine nucleotide. In the case of A analogues, the modifications may be a modification to the A base to give analogues which have a lower efficiency of incorporation than non modified adenosine analogues.

Within the scope of the invention is a method of amplifying a plurality of template nucleic acids having different sequences by repeatedly copying the template nucleic acids in the presence of non-extendable nucleotide analogues. The non-extendable nucleotide analogues in an amplification reaction can be of one or more type such that they are capable of base-pairing with one or more type of base in the template nucleic acid. Typically, the variety of non-extendable nucleotide analogue types is limited to exclude base-pairing with at least one type of base in the template. For example, an amplification reaction can include non-extendable nucleotide analogues that are capable of base-pairing with A and/or T bases in a template, but the amplification reaction can lack non-extendable nucleotide analogues that are capable of base-pairing with G and/or C bases in a template. Extendable nucleotides or extendable nucleotide analogues are typically also present in the amplification reaction. Also, the relative amount of a non-extendable nucleotide analogue that base-pairs with a particular base in a template is typically low compared to the amount of extendable nucleotide (or nucleotide analogue) that base-pairs with the same base in the template. However, it will be understood that the appropriate amount of a non=extendable nucleotide analogue may be determined empirically. The amplification products of the template nucleic acids having a high level of the nucleotides which are partially replaced with the non-extendable analogues become deficient in representation.

Methods of the invention may make use of non-extendable nucleotides which act as terminators and prevent further strand elongation. Such terminators may be permanent (for example dideoxyribose analogues such as ddTTP or ddATP) or reversible. Reversible terminators may contain any moiety which acts to block polymerase extension, but can subsequently be altered to allow polymerase extension. Suitable reversible terminator moieties include blocking groups on the nucleotide 3' hydroxyl. There are many known 3' hydroxyl blocking moieties which are capable of acting as reversible polymerase blocks, including the allyl, methoxymethyl, azidomethyl or O—NH$_2$ groups. Further examples of terminator moieties may be attached to the nucleotide base, 2' or 4' positions. Examples of nucleoside terminators can be found in U.S. Pat. No. 5,302,509, U.S. Pat. No. 7,057,026, U.S. Pat. No. 6,664,079, U.S. Pat. No. 7,541,444 and U.S. Pat. No. 7,544,794 the contents of which are incorporated by reference herein in their entirety. Reversible terminators may be removed to allow subsequent polymerase action on the strands, for example to synthesise full length strands at the end of the amplification process.

In combination with certain polymerases, uracil analogues can function to prevent or slow down strand elongation. Replacement of a portion of the thymine with uracil bases on nucleotides can hence be used to inhibit or slow down the amplification of AT rich sequences. Archeal polymerases, for example Pfu polymerase shows a lower ability to incorporate dUTP and extend beyond uracil bases than conventional polymerases. Thus the partial replacement of dTTP with dUTP can act to lower the efficiency and/or rate of amplification of AT rich sequences. The partial substitution of dTTP with dUTP may be more effective when an archeal polymerase is used. The archaeal polymerase may be Pfu polymerase, or a derivative thereof.

Alternative nucleoside analogues that can be used in a method set forth herein are those where the phosphate portion of the 5' polyphosphate is altered. For example, a number of nucleoside triphosphate analogues which lower the rate of polymerase incorporation are known. Analogues where one or more of the oxygen atoms in the triphosphate are replaced with sulfur, $CH_2$ or $CF_2$ serve to make the amplification process less efficient.

Also provided herein is a method for normalising the amplification of nucleic acid templates of different sequence using an additive. The additives described herein are related at least for their ability to normalise amplification of nucleic acid templates of different sequence. For example, the additives described herein function similarly to normalise amplification, at least, by increasing the efficiency of amplification of GC rich templates or decreasing the efficiency of amplification of AT rich templates. The methods optionally include the use of different concentrations of nucleotides and/or nucleotide analogs as described herein. The additives may be, for example, ethylene glycol, polyethylene glycol, 1,2-propanediol, dimethyl sulfoxide (DMSO), glycerol, formamide, 7-deaza-GTP, acetamide, tetramethyl ammonium chloride (TMAC1), salt or betaine. For example, betaine (carboxymethyl trimethyl ammonium $((CH_3)_3N^+CH_2COO^-)$) may be added to the amplification mix in order to normalise the amplification of different template sequences. Optionally, a combination of betaine and DMSO or a combination of betaine, DMSO and 7-deaza-dGTP is used. Concentrations of betaine may be above 2 Molar (M), for example, between 2 and 5 M, between 2.5 and 4 M or between 2.75 and 3.75 M. Suitable concentrations of betaine include, but are not limited to, 2.5, 3, 3.25, 3.5, 3.75 or 4 M. Higher concentrations of betaine may cause the inhibition of AT rich templates at a proportionally higher level than inhibition of GC rich templates. Under certain conditions, very high levels of betaine may be used to inhibit all amplification.

Also provided is a method for amplifying nucleic acid templates of different sequence comprising a first round comprising one or more cycles of amplification, wherein the cycles of amplification comprise amplifying the nucleic acid templates under conditions favouring AT rich templates, for example, as compared to a control; and a second round comprising one or more cycles of amplification, wherein the cycles of amplification comprise amplifying the nucleic acid templates under conditions favouring GC rich templates, for example, as compared to a control.

As used throughout, the term "round" includes one or more cycles of amplification. The term "cycle of amplification" refers to one or more steps of an amplification process that are sufficient to produce one or more copies of a nucleic acid template. By way of example, a cycle of amplification includes providing one or more nucleic acid templates, denaturing the nucleic acid templates to produce single stranded nucleic acid templates, annealing one or more primers to the single stranded nucleic acid templates, and extending the primers to produce copies of the single stranded nucleic acid templates. As described herein, such cycles can be repeated one or more times under conditions favouring AT rich or GC rich templates. Thus, a cycle of amplification can include a unit of one or more steps that is repeated in a round of amplification.

In the methods, the first or second round, optionally, comprises one to fifty, one to twenty-five, one to fifteen, or one to ten cycles of amplification. Optionally, the first round comprises one, five, ten, fifteen, twenty, or twenty-five cycles of amplification and the second round comprises one, five, ten, fifteen, twenty or twenty-five cycles of amplification.

Optionally, the nucleic acid templates are immobilized. Optionally, the nucleic acid templates are immobilized on a solid support, for example, a resin, gel, bead, well, column, chip, membrane, matrix, plate, or filter.

In the provided methods, the concentration of dATP or dTTP in the second round, optionally, is less than the concentration of dGTP and dCTP in the first round. Optionally, the concentration of dATP or dTTP is less than half, one quarter or one tenth the concentration of dGTP and dCTP. Optionally, the concentration of dATP or dTTP is less than 20 or less than 10 micromolar. Optionally, the second round includes the use of a T or A nucleotide analogue. Optionally, the T or A analogue acts as a strand terminator. Optionally, dUTP is used as a partial replacement for dTTP. Optionally, the T analogue is 2-thio dTTP. Such methods of amplification using nucleotides at different concentrations and nucleotide analogues are described further throughout.

Optionally, as described herein, the second round includes the use of one or more additives. Optionally, the additive is ethylene glycol, polyethylene glycol, 1,2-propanediol, dimethyl sulfoxide (DMSO), glycerol, formamide, 7-deaza-dGTP, acetamide, betaine or tetramethylammonium chloride (TMACL). Optionally, the betaine is present at a concentration of 2.5, 3, 3.25, 3.5, 3.75 or 4M. Optionally, a combination of betaine and DMSO or betaine, DMSO and 7-deaza-dGTP is used.

Optionally, the annealing temperature in the second round is higher than the annealing temperature in the first round. Optionally, the annealing temperature in the second round is 55-65° C., Optionally, the annealing temperature in the second round is 58-62° C.

Optionally, the concentration of salt in the first round is lower than the concentration of salt in the second round. For example, the concentration of salt in the first round can be 1.25×, 1.5×, 2×, 2.5×, 3×, 3.5×, 4×, 4.5×, 5× or greater than 5×, lower than the concentration of salt in the second round. Stated another way the concentration of salt is higher in the second round than the first round. The concentration of salt can be increased in the second round by addition of KCl.

Optionally, the pH in the first round is higher than the pH in the second round. For example, the pH in the first round can be 1.25×, 1.5×, 2×, 2.5×, 3×, 3.5×, 4×, 4.5×, 5× or greater than 5×, higher than the pH in the second round.

Optionally, the ionic strength in the first round is lower than the ionic strength in the second round. For example, the ionic strength in the first round can be 1.25×, 1.5×, 2×, 2.5×, 3×, 3.5×, 4×, 4.5×, 5× or greater than 5× lower than the ionic strength in the second round.

Optionally, the first round occurs prior to the second round. Optionally, the second round occurs prior to the first round. The first and second rounds can be repeated one or more times.

As used throughout, the phrase "favouring AT rich templates" means that the efficiency of amplification of AT rich templates is not reduced or inhibited relative to non-AT rich templates. By way of example, under standard amplification conditions, AT rich templates amplify at a higher efficiency than GC rich templates. Thus, conditions favouring AT rich templates include standard amplification conditions. As used throughout, the phrase standard amplification conditions means amplifying a nucleic acid sequence under conditions including all standard reagents and conditions necessary to carry out amplification. Standard amplification conditions are known and described in, for example, Saiki et al., *Science,* 20:1350 (1985).

As used herein, the phrase "favouring GC rich templates" means that the efficiency of amplification of GC rich templates is increased relative to AT rich templates and/or the efficiency of amplification of AT rich templates is reduced relative to GC rich templates.

As used herein, the terms high, higher, increase(s), increased, or increasing refer to any increase above a reference or control, unless stated otherwise. The terms low, lower, decrease(s), decreased, decreasing, reduce(s), reduced, reducing or reduction refer to any decrease below a reference or control, unless stated otherwise. By way of example, a control includes control values or control levels, which can be values or levels prior to, or in the absence of, a stimulus. A control or control value includes the level of efficiency of amplification of nucleic acid sequences under standard amplification conditions or can comprise a known value, level or standard. Thus, for example, a higher or lower value (e.g., temperature or concentration) as compared to a control refers to a value that is higher or lower than a known or arbitrarily set value.

The methods set forth herein may be carried out on a solid support. In the case of amplification reactions carried out on a solid support, it is possible to perform multiple cycles of amplification using different reagent compositions in each cycle, as described above. In the case of cluster amplification, where each nucleic acid copy in the cluster is amplified from a single molecule, it may be advantageous to perform the first cycles (e.g., 1-5 cycles) in the first round using an equimolar concentration of four nucleotides, and then, in the second round, switch during later cycles of amplification to conditions wherein the efficiency of copying AT rich sequences is decreased. By way of example, it is possible to carry out the methods described herein wherein the early cycles in the first round are carried out using four different nucleotide types that are present at the same concentration, followed, in the second round, by cycles where the four different nucleotide types are present in an imbalanced or skewed concentration. It is also possible to carry out the early cycles in the first round using four different nucleotide types that are present at the same concentration, then switching, in the second round, to reaction conditions including nucleotide analogues which are incorporated less efficiently, or nucleotides which act as terminators, for later cycles. Furthermore, the ratio of the skewed nucleotides may be altered between different cycles in the second round.

By way of another example, the first cycles in the first round are carried out using four different nucleotide types present at the same concentration, followed, in the second round, by cycles including one or more additives, for example, betaine and/or DMSO.

The present disclosure provides a solid support, nucleic acids templates and a solution of nucleotides that are useful in carrying out a method set forth herein. In the cases of amplification using four types of nucleotides, the four nucleotide types might not be present at equimolar concentrations. In cases where the nucleic acid templates comprise multiple different sequences, the ratio of the number of molecules and/or the physical sizes of the GC rich and AT rich templates may be approximately equal. The composition may contain the four nucleotides triphosphates dATP, dCTP, dGTP and dTTP. The composition may additionally contain any of the nucleotide analogues described above as full or partial replacements for any one of the four nucleotides.

The ratios of the nucleotides in a composition set forth herein may be varied according to the proportions described above. Thus for example the composition may have less dATP and/or dTTP than dCTP and dGTP. The concentration of dATP may be less than half, less than one quarter, less than one tenth, or lower than the individual concentration of dGTP or dCTP. The concentration of dTTP may be less than half, less than one quarter, less than one tenth, or lower than the individual concentration of dGTP or dCTP. The concentration of dATP may be the same as the concentration of dTTP, which may be lower than the individual concentration of dCTP or dGTP. A composition set forth herein may contain a concentration of dATP less than 20 micromolar, or a concentration of dTTP less than 20 micromolar. The composition may contain a concentration of dATP less than 10 micromolar, or a concentration of dTTP less than 10 micromolar.

The amplification methods described herein may be carried out thermally or isothermally. Thermal cycling involves changes in temperature to denature the extended double stranded template product and anneal new primers. The term "isothermal" refers to thermodynamic processes in which the temperature of a system remains constant: $\Delta T=0$. This typically occurs when a system is in contact with an outside thermal reservoir (for example, heat baths and the like), and processes occur slowly enough to allow the system to continually adjust to the temperature of the reservoir through heat exchange.

The term "substantially isothermal" as used herein is intended to mean that the system is maintained at essentially the same temperature. The term is also intended to capture minor deviations in temperature which might occur as the system equilibrates, for example when components which are of lower or higher temperature are added to the system. Thus it is intended that the term includes minor deviations from the temperature initially chosen to perform the method and those in the range of deviation of commercial thermostats. Particularly the temperature deviation will be no more than about +/−2° C., more particularly no more than about +/−1° C., yet more particularly no more than about +/−0.5° C., no more than about +/−0.25° C., no more than about +/−0.1° C. or no more than about +/−0.01° C.

The term "amplifying" as used herein is intended to mean the process of increasing the numbers of a template polynucleotide sequence by producing one or more copies. Accordingly it will be clear that the amplification process can be either exponential or linear. In exponential amplification the number of copies made of the template polynucleotide sequence increases at an exponential rate. For example, in an ideal PCR reaction with 30 cycles, 2 copies of template DNA will yield $2^{30}$ or 1,073,741,824 copies. In linear amplification the number of copies made of the template polynucleotide sequences increases at a linear rate. For example, in an ideal 4-hour linear amplification reaction whose copying rate is 2000 copies per minute, one molecule of template DNA will yield 480,000 copies.

The term "copy" when used in reference to a first nucleic acid molecule is intended to mean a second nucleic acid molecule having the same sequence as the first nucleic acid or the complementary sequence of the nucleic acid. The nucleic acids can be single stranded or double stranded. For example, a single stranded copy can have the same sequence of a single stranded template, a single stranded copy can have the complementary sequence of a single stranded template, a double stranded copy can include the same sequence and the complementary sequence (i.e. two strands) of a single stranded template, or a double stranded copy can include the same sequences as a double stranded template. Similarly, the term "copy" when used in reference to a nucleic acid sequence means the same sequence or the complementary sequence.

As used herein, the terms "polynucleotide", "oligonucleotide" or "nucleic acid" can refer to deoxyribonucleic acid (DNA), ribonucleic acid (RNA) or analogues of either DNA or RNA made, for example, from nucleotide analogues. The terms "polynucleotide", "oligonucleotide" or "nucleic acid" are applicable to single stranded (such as sense or antisense) and double stranded molecules. The terms "polynucleotide", "oligonucleotide" or "nucleic acid" as used herein also encompass cDNA, that is complementary or copy DNA produced from an RNA template, for example by the action of reverse transcriptase.

Single stranded polynucleotide molecules useful in a method or composition of the invention may have originated in single-stranded form, as DNA or RNA or may have originated in double-stranded DNA (dsDNA) form (e.g. genomic DNA fragments, PCR and amplification products and the like). Thus a single stranded polynucleotide may be the sense or antisense strand of a polynucleotide duplex. Methods of preparation of single stranded polynucleotide molecules suitable for use in the method of the invention using standard techniques are well known in the art.

In a particular embodiment, single stranded polynucleotide molecules are DNA molecules. More particularly, the polynucleotide molecules represent the entire genetic complement of an organism, for example plants, bacteria, viruses, mammals, and are genomic DNA molecules which include both intron and exon sequence (coding sequence), as well as non-coding regulatory sequences such as promoter and enhancer sequences. Although it could be envisaged that particular sub-sets of polynucleotide sequences or genomic DNA could also be used, such as particular chromosomes, for example. Yet more particularly, the sequence of the polynucleotide molecules is not known. Still yet more particularly, the polynucleotide molecules are human genomic DNA molecules.

The sequence of polynucleotide molecules made or used as set forth herein may be the same as each other or different from each other. For example, a mixture of polynucleotide molecules of different sequences may be prepared by mixing a plurality, greater than one, of individual primary polynucleotide molecules. For example, DNA from more than one source can be prepared if each DNA sample is first tagged to enable its identification after it has been sequenced. Many different suitable DNA-tag methodologies already exist in the art, for example as described in WO 05/068656, which is incorporated herein by reference, and are well within the purview of the skilled person.

Single stranded polynucleotide molecules to be amplified (referred to as templates) can originate as duplexes or single strands. For ease of reference, single stranded templates are described herein, as the duplexes often need to be denatured prior to amplification. When viewed as a single strand, the 5' ends and the 3' ends of one strand of the template duplex may comprise different sequences, herein depicted as Y and Z for ease of reference. The other strand will usually be amplified in any amplification reaction, but would comprise sequence Z' at the 5' end and Y' at the 3' end, where Z' is the complement of Z, and Y' is the complement of Y. This strand may be present in many or all of the processes described herein, but is not further discussed.

In a particular embodiment, a single stranded polynucleotide molecule has two regions of known sequence. Yet more particularly, regions of known sequence will be at the 5' and 3' termini of the single stranded polynucleotide molecule such that the single stranded polynucleotide molecule will be of the structure:

5' [known sequence I]-[target polynucleotide sequence]-[known sequence II]-3'.

Typically "known sequence I" and "known sequence II" may consist of more than 20, or more than 40, or more than 50, or more than 100, or more than 300 consecutive nucleotides. The precise length of the two sequences may or may not be identical. Known sequence I may comprise a region of sequence Y, which may also be the sequence of one of the immobilised primers. Known sequence II may comprise a region of sequence Z, which hybridises to sequence X, which may be the sequence of another of the immobilised primers. Known sequences I and II may be longer than sequences Y and Z used to hybridise to the immobilised amplification primers.

In a first amplification step, a solid support having immobilised thereon single stranded polynucleotide molecules and a plurality of primer oligonucleotides may be provided. The term "immobilised" as used herein is intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to a support under conditions in which it is intended to use the support, for example in applications requiring nucleic acid amplification and/or sequencing.

The term "solid support" as used herein refers to any surface, inert substrate or matrix to which nucleic acids can be attached such as, for example, beads, including latex or dextran beads, a surface, such as a polystyrene or polypropylene surface, polyacrylamide gel, gold surfaces, glass surfaces and silicon wafers. The solid support may be a glass surface. The solid support may be a planar surface, although the invention also works on beads which are moved between containers of different buffers, or beads arrayed on a planar surface. The solid support can be a resin, gel, head, well, column, chip, flowcell, membrane, matrix, plate or filter.

In certain embodiments the solid support may comprise an inert substrate or matrix which has been "functionalised", for example by the application of a layer or coating of an intermediate material comprising reactive groups which permit covalent attachment to molecules such as polynucleotides. By way of non-limiting example such supports may include polyacrylamide hydrogels supported on an inert substrate such as glass. In such embodiments the molecules (e.g. polynucleotides) may be directly covalently attached to the intermediate material (e.g. the hydrogel) but the intermediate material may itself be non-covalently attached to the substrate or matrix (e.g. the glass substrate). Such an arrangement is described more fully in co-pending application WO 05/065814, whose contents are included herein by reference.

Primer oligonucleotides or primers are polynucleotide sequences that are capable of annealing specifically to one or more single stranded polynucleotide template to be amplified under conditions encountered in the primer annealing step of each cycle of an amplification reaction. Generally amplification reactions can use at least two amplification primers, often denoted "forward" and "reverse" primers. In certain embodiments the forward and reverse primers may be identical. The forward primer oligonucleotides can include a "template-specific portion", being a sequence of nucleotides capable of annealing to a primer-binding sequence in at least one strand of the molecule to be amplified. Reverse primer oligonucleotides can include a template specific portion capable of annealing to the complement of the strand to which the forward primer anneals during the annealing step. The primer binding sequences generally will be of known sequence. In some embodiments the primer binding sequences can be complementary to a sequence within known sequence I and/or known sequence II of the single stranded polynucleotide molecule. The length of the primer binding sequences Y and Z need not be the same as those of known sequence I or II, and are preferably shorter, being particularly 16-50 nucleotides, more particularly 16-40 nucleotides and yet more particularly 20-30 nucleotides in length. The optimum length of the primer oligonucleotides will depend upon a number of factors and in particular embodiments it is preferred that the primers are long (complex) enough so that the likelihood of annealing to sequences other than the primer binding sequence is very low.

Generally primer oligonucleotides are single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand.

Primers may additionally comprise non-nucleotide chemical modifications, again provided that such modifications do not permanently prevent primer function. Chemical modifications may, for example, facilitate covalent attachment of the primer to a solid support. Certain chemical modifications may themselves improve the function of the molecule as a primer, or may provide some other useful functionality, such as providing a site for cleavage to enable the primer (or an extended polynucleotide strand derived therefrom) to be cleaved from a solid support.

Although the invention may encompass solid-phase amplification methods, in which only one amplification primer is immobilised on a solid support (the other primer usually being present in free solution), in a particular embodiment, the solid support may be provided with both the forward and reverse primers immobilised. In practice there can be a plurality of identical forward primers and/or a plurality of identical reverse primers immobilised on the solid support, for example, in embodiments wherein the amplification process utilizes an excess of primers to sustain amplification. Thus references herein to forward and reverse primers are to be interpreted accordingly as encompassing a plurality of such primers unless the context indicates otherwise.

"Solid-phase amplification" as used herein refers to any nucleic acid amplification reaction carried out on or in association with a solid support such that all or a portion of the amplified products are immobilised on the solid support. In particular, the term encompasses solid phase amplification reactions analogous to standard solution phase PCR except that one or both of the forward and reverse amplification primers is/are immobilised on the solid support.

As will be appreciated by the skilled reader, many types of amplification reactions utilize at least one type of forward primer and at least one type of reverse primer specific for the template to be amplified. However, in certain embodiments the forward and reverse primers may comprise template specific portions of identical sequence, and may have entirely identical nucleotide sequence and structure (including any non-nucleotide modifications). In other words, it is possible to carry out solid phase amplification using only one type of primer, and such single primer methods are encompassed within the scope of the invention. Other embodiments may use forward and reverse primers which contain identical template-specific sequences but which differ in some other structural features. For example, one type of primer may contain a non-nucleotide modification which is not present in the other. In still yet another embodiment the template-specific sequences are different and only one primer is used in a method of linear amplification.

In other embodiments of the invention the forward and reverse primers may contain template-specific portions of different sequence.

Alternative embodiments of the invention may include any method to amplify nucleic acids, for example rolling circle amplification, random primer amplification, or amplification using a helicase or recombinase. Rolling circle amplification can be used to make long linear amplicons where a certain sequence is repeated. The methods of the invention described herein may be used to normalise the length of the linear region of the amplicon, and to minimise the over-amplification of certain sequences. The RCA reaction may be carried out on a solid support, or the amplicons may be formed in solution. The amplicons may be subsequently immobilised on a solid support. Recombinase/polymerase amplification (RPA) is described in more detail in granted patent U.S. Pat. No. 7,270,981, the contents of which are incorporated herein by reference in their entirety, and RPA with a skewed ratio of nucleotides is within the scope of the invention.

In many embodiments of the invention, amplification primers for solid phase amplification are immobilised by covalent attachment to a solid support at or near the 5' end of the primer, leaving the template-specific portion of the primer free to anneal to its cognate template and the 3' hydroxyl group free to function in primer extension. The chosen attachment chemistry will depend on the nature of the solid support, and any functionalisation or derivitisation applied to it. The primer itself may include a moiety, which may be a non-nucleotide chemical modification to facilitate attachment. In particular embodiments the primer may include a sulphur containing nucleophile such as phosphothioate or thiophosphate at the 5' end. In the case of solid supported polyacrylamide hydrogels, this nucleophile may bind to a bromoacetamide group present in the hydrogel. In a preferred embodiment the means of attaching the primers to the solid support is via 5' phosphothioate attachment to a hydrogel comprised of polymerised acrylamide and N-(5-bromoacetamidylpentyl) acrylamide (BRAPA). Such an arrangement is described more fully in co-pending application WO 05/065814, whose contents are incorporated herein by reference.

Single stranded template polynucleotide molecules may be attached to a solid support via hybridisation to immobilised primers, or alternatively the single stranded polynucleotide molecules may also be directly attached to the solid support at or near the 5' end. The chosen attachment chemistry will depend on the nature of the solid support, and any functionalisation or derivitisation applied to it. The single stranded polynucleotide molecule itself may include a moiety, which may be a non-nucleotide chemical modification to facilitate attachment. In particular embodiments a single stranded polynucleotide molecule may include a sulphur containing nucleophile such as phosphorothioate or thiophosphate at the 5' end. In the case of solid supported polyacrylamide hydrogels, this nucleophile can also bind to the bromoacetamide groups present in the hydrogel. In one embodiment the means of attaching the single stranded polynucleotide molecule to the solid support is via 5' phosphorothioate attachment to a hydrogel comprised of polymerised acrylamide and N-(5-bromoacetamidylpentyl) acrylamide (BRAPA). Such an arrangement is described more fully in co-pending application WO 05/065814, whose contents are incorporated herein by reference.

The distance between individual primer oligonucleotides and one or more single stranded template polynucleotide molecules (and hence the density of the primer oligonucleotides and single stranded polynucleotide molecules) can be controlled by altering the concentration of primer oligonucleotides and single stranded polynucleotide molecules that are immobilised to the support. A preferred density of primer oligonucleotides is at least 1 fmol/mm$^2$, preferably at least 10 fmol/mm$^2$, more preferably between 30 to 60 fmol/mm$^2$. The density of single stranded polynucleotide molecules for use in the method of the invention is typically 10,000/mm$^2$ to 100,000/mm$^2$. Higher densities, for example, 100,000/mm$^2$ to 1,000,000/mm$^2$ and 1,000,000/mm$^2$ to 10,000,000/mm$^2$ may also be achieved.

Controlling the density of single stranded polynucleotide molecules and primer oligonucleotides in turn allows the final density of nucleic acid colonies on the surface of the support to be controlled. This is due to the fact that according to particular methods of the invention, one nucleic acid colony can result from the attachment of one single stranded polynucleotide molecule, providing the primer oligonucleotides of the invention are present in a suitable location on the solid support. The density of single stranded polynucleotide molecules within a single colony can also be controlled by controlling the density of attached primer oligonucleotides. The relative number of strands in each colony can be controlled by the methods described herein such that the colonies of different sequence each contain similar numbers of nucleic acid strands, and occupy similar areas of the surface.

In one embodiment of the invention, a complementary copy of a single stranded polynucleotide molecule is attached to a solid support by a method of hybridisation and primer extension. Methods of hybridisation for formation of stable duplexes between complementary sequences by way of Watson-Crick base-pairing are known in the art. The single stranded template may originate from a duplex that has been denatured in solution, for example by sodium hydroxide or formamide treatment then diluted into a suitable hybridisation buffer. The template may be hybridised to the surface at a temperature different to that used for subsequent amplification cycles. The immobilised primer oligonucleotides can hybridise at and can be complementary to a region or template specific portion of the single stranded polynucleotide molecule. An extension reaction may then be carried out wherein the primer is extended by sequential addition of nucleotides to generate a complementary copy of the single stranded polynucleotide sequence attached to the solid support via the primer oligonucleotide. The single stranded polynucleotide sequence not immobilised to the support may be separated from the complementary sequence under denaturing conditions and removed, for example, by washing with hydroxide or formamide. The primer used for initial primer extension of a hybridised template may be one of the forward or reverse primers used in the amplification process. After an initial hybridisation, extension and separation, an immobilised template strand is obtained.

In yet another embodiment a single stranded polynucleotide molecule can be ligated to primers immobilised to a solid support using ligation methods known in the art and standard methods (Sambrook and Russell, Molecular Cloning, A Laboratory Manual, third edition). Such methods can utilise ligase enzymes such as DNA ligase to effect or catalyse joining of the ends of the two polynucleotide strands of, in this case, the single stranded polynucleotide molecule and the primer oligonucleotide such that covalent linkages are formed. In this context, joining means covalent linkage of two polynucleotide strands which were not previously covalently linked.

In a particular aspect of the invention, such joining takes place by formation of a phosphodiester linkage between the two polynucleotide strands. However, other means of covalent linkage (e.g. non-phosphodiester backbone linkages) may be used. Another equally applicable method is splicing by overlap extension (SOE). In SOE, polynucleotide molecules are joined at precise junctions irrespective of nucleotide sequences at the recombination site and without the use of restriction endonucleases or ligase. Fragments from the polynucleotide molecules that are to be recombined are generated by methods known in the art. The primers are designed so that the ends of the products contain complementary sequences. When these polynucleotide molecules are mixed, denatured, and reannealed, the strands having the matching sequences at their 3' ends overlap and act as primers for each other. Extension of this overlap by DNA polymerase produces a molecule in which the original sequences are 'spliced' together. The method, for example, as disclosed by Horton et al (Gene. 1989 Apr. 15; 77(1):61-8) may also potentially be performed isothermally.

Primer oligonucleotides and single stranded polynucleotide molecules that have been immobilised on a solid support at a desired density can be used to generate extension products by carrying out an appropriate number of cycles of amplification on the covalently bound single stranded polynucleotide molecules so that each colony, or cluster comprises multiple copies of the original immobilised single stranded polynucleotide molecule (and its complementary sequence). One cycle of amplification can include steps of hybridisation, extension and denaturation. Such steps are generally comparable with the steps of hybridisation, extension and denaturation of PCR.

In embodiments utilizing solid phase amplification, suitable conditions can be applied to a single stranded polynucleotide molecule and a plurality of immobilized primer oligonucleotides such that sequence Z at the 3' end of the single stranded polynucleotide molecule hybridises to a primer oligonucleotide sequence X to form a complex wherein, the primer oligonucleotide hybridises to the single stranded template to create a 'bridge' structure. Suitable conditions such as neutralising and/or hybridising buffers are well known in the art (See Sambrook et al., Molecular Cloning, A Laboratory Manual, $3^{rd}$ Ed, Cold Spring Harbor Laboratory Press, NY; Current Protocols, eds Ausubel et al.). The neutralising and/or hybridising buffer may then be removed. One suitable hybridisation buffer is referred to as 'amplification pre-mix', and contains 2 M betaine, 20 mM Tris, 10 mM Ammonium Sulfate, 2 mM Magnesium sulfate, 0.1% Triton, 1.3% DMSO, pH 8.8.

By applying suitable conditions, an extension reaction can be performed for a complex formed between immobilized primer and single stranded polynucleotide template. The primer oligonucleotide of the complex can be extended by sequential addition of nucleotides to generate an extension product complementary to the single stranded polynucleotide molecule.

Suitable conditions such as extension buffers/solutions comprising an enzyme with polymerase activity are described herein in order to minimise variations in the amplification efficiencies of different nucleic acid sequences. In a particular embodiment dNTPs at different ratios may be included in the extension buffer for one or more of the amplification cycles. In a further embodiment terminators or nucleotides analogues are included as a partial or complete replacement for one or more of the dNTPs. Variations in amplification efficiencies of different nucleic acid sequences can also be minimised using additives, changes in temperature (e.g., annealing temperature), pH, and/or ionic strength.

Examples of enzymes with polymerase activity which can be used in the present invention are DNA polymerase (Klenow fragment, T4 DNA polymerase, Bst polymerase), heat-stable DNA polymerases from a variety of thermostable bacteria (such as Taq, VENT, Pfu, Tfl DNA polymerases) as well as their genetically modified derivatives (TaqGold, VENTexo, Pfu exo). A combination of RNA polymerase and reverse transcriptase can also be used to generate the extension products. A useful polymerase enzyme can have strand displacement activity. The polymerase enzyme can be active at a pH of about 7 to about 9, particularly pH 7.9 to pH 8.8. The nucleoside triphosphate molecules used can be deoxyribonucleotide triphosphates, for example dATP, dTTP, dCTP, dGTP, or they can be ribonucleoside triphosphates for example ATP, UTP, CTP, GTP. The nucleoside triphosphate molecules may be naturally or non-naturally occurring. An amplification reaction may also contain additives such as DMSO and or betaine, for example, to normalise the melting temperatures of the different sequences in the template strands. A suitable solution for initial cycles of extension is referred to as 'amplification mix' and contains 2 M betaine, 20 mM Tris, 10 mM Ammonium Sulfate, 2 mM Magnesium sulfate, 0.1% Triton, 1.3% DMSO, pH 8.8 plus 200 µM dNTPs and 80 units/mL of Bst polymerase (NEB Product ref M0275L). After a chosen number of cycles with equimolar concentrations of dNTPs, the ratio of dNTPs can be skewed, for example using 10 µM dATP, 10 µM dTTP 390 µM dCTP and 390 µM dGTP. Alternatively, a skewed ratio can be used in each cycle of the amplification reaction.

After hybridisation and extension steps have been carried out on a solid support, the support and attached nucleic acids can be subjected to denaturation conditions. Preferably the extension buffer is first removed. The denaturation can be carried out using heat or by using a denaturing buffer. Suitable denaturing buffers are well known in the art (See Sambrook et al., Molecular Cloning, A Laboratory Manual, 3$^{rd}$ Ed, Cold Spring Harbor Laboratory Press, NY; Current Protocols, eds. Ausubel et al.). By way of example it is known that alterations in pH and low ionic strength solutions can denature nucleic acids at substantially isothermal temperatures. Formamide and urea can be used for denaturation. In a particular embodiment the concentration of formamide is 50% or more, and may be used neat. Such conditions result in denaturation of double stranded nucleic acid molecules to single stranded nucleic acid molecules. Alternatively or additionally, the strands may be separated by treatment with a solution of very low salt (for example less than 0.1 mM cationic conditions) and high pH (>12) or by using a chaotropic salt (e.g. guanidinium hydrochloride). In a particular embodiment, a strong base may be used. A strong base is a basic chemical compound that is able to deprotonate very weak acids in an acid base reaction. The strength of a base is indicated by its $pK_b$ value. Compounds with a $pK_b$ value of less than about 1 are called strong bases and are well known to a skilled practitioner. In a particular embodiment the strong base is Sodium Hydroxide (NaOH) solution used at a concentration of from 0.05 M to 0.25 M. More particularly NaOH is used at a concentration of 0.1 M.

Following denaturation, two immobilised nucleic acids are produced from a double stranded nucleic acid molecule. In solid-phase amplification embodiments, the first strand may be the initial immobilised single stranded polynucleotide template molecule and the second strand may be a nucleic acid complementary thereto, extending from an immobilised primer oligonucleotide, comprising sequence Z' at the 5' end. Both the original immobilised single stranded polynucleotide molecule and the immobilised extended primer oligonucleotide formed are then able to initiate further cycles of amplification on subjecting the support to further cycles of hybridisation, extension and denaturation by hybridisation to primer sequences Z' and Y respectively.

It may be advantageous to perform optional washing steps in between steps of an amplification method. For example, an extension buffer without polymerase enzyme with or without dNTPs could be applied to a solid support upon which amplification is being carried out and it can be applied before being removed and replaced with complete extension buffer (extension buffer that includes all necessary components for extension to proceed).

Multiple cycles of amplification on a solid surface under conditions exemplified above can result in a nucleic acid colony or "cluster" comprising multiple immobilised copies of a particular single stranded polynucleotide sequence and its complementary sequence. Initial immobilisation of a single stranded polynucleotide molecule under conditions exemplified herein can result in the single stranded polynucleotide molecule only hybridising with primer oligonucleotides located at a distance within the total length of the single stranded polynucleotide molecule. Thus, the boundary of the nucleic acid colony or cluster formed can be limited to a relatively local area, namely the area in which the initial single stranded polynucleotide molecule was immobilised. If conditions are used wherein the templates and the complementary copies thereof remain immobilised throughout the whole amplification process, then the templates do not become intermingled other than by becoming large enough to overlap on the surface. In particular embodiments, there is no non-immobilised nucleic acid during any part of the amplification process, and thus the templates cannot diffuse and initiate further clusters elsewhere on the surface.

An amplification process may entail cycles of exposure to conditions for hybridisation, extension and denaturation of nucleic acid sequences. The cycles may be repeated in order to obtain a sufficient level of amplification. The amplification process (e.g., in a round) may be carried using, for example, 10, 15, 20, 25, 30, 35, 40 or 45 or more cycles of amplification. Each cycle may be carried out using the same reagents and conditions, or the reagents and/or conditions, may be varied between different cycles. For example, the first 5, 10, 15, 20 or 25 cycles, in a first round, may be carried out using extension conditions with equimolar concentrations of four different nucleotide types, and subsequent cycles, in a second round, may be carried out using conditions resulting in less efficiently incorporated nucleotides. Normalised amplification conditions using less efficiently incorporated nucleotides can be used. An increased number of amplification cycles can be carried out, as the overall efficiency of amplification is reduced, and the AT rich sequences do not become over-amplified. It is therefore possible to carry out, for example, 25 cycles of amplification in a first round using equimolar nucleotide concentrations, and 15 or more additional cycles of amplification in a second round using conditions using nucleotides incorporated with lower efficiency (for example limited concentrations of A and/or T nucleotides). Such additional cycles in the second round amplify the GC rich clusters preferentially to the AT rich clusters, hence normalising the intensity of clusters of different sequence compositions.

Once more copies of a single stranded polynucleotide molecule and its complement have been synthesised by carrying out multiple cycles of amplification, i.e., multiple cycles of hybridisation, extension and denaturation, then the boundary of the nucleic acid colony or cluster being generated is extended further. However, the boundary of the colony formed is typically still limited to a relatively local area, essentially in the vicinity of the area in which the initial single stranded polynucleotide molecule was immobilised. Clusters may be of a diameter of 100 nm to 10 □m, a higher information density being obtainable from a typical clustered array where the clusters are of a smaller size.

It can thus be seen that a method of the present invention can allow for the generation of a nucleic acid colony from a single immobilised single stranded polynucleotide molecule and that the size or mass of these colonies can be controlled by altering the conditions during rounds containing one or more cycles of amplification to which the single stranded polynucleotide molecule is subjected.

Hybridisation, extension and denaturation steps of an amplification method set forth herein may all be carried out at the same, substantially isothermal temperature. Preferably the temperature is from 37° C. to about 75° C., depending on the choice of enzyme, more preferably from 50° C. to 70° C., yet more preferably from 60° C. to 65° C. for Bst polymerase. In a particular embodiment the substantial isothermal temperature may be around the melting temperature of the oligonucleotide primer(s) Methods of calculating appropriate melting temperatures are known in the art. For example the annealing temperature may be about 5° C. below the melting temperature (Tm) of the oligonucleotide primers. In yet another particular embodiment the substantially isothermal temperature may be determined empirically. The temperature can be that at which the oligonucleotide displays greatest specificity for the primer binding site whilst reducing non-specific binding.

Thus, in particular embodiments, the number of nucleic acid colonies or clusters formed on the surface of a solid support may dependent upon the number of single stranded polynucleotide molecules which are initially immobilised to the support, providing there are a sufficient number of immobilised primer oligonucleotides within the locality of each immobilised single stranded polynucleotide molecule. It is for this reason that the solid support to which the primer oligonucleotides and single stranded polynucleotide molecules have been immobilised may comprise a lawn of immobilised primer oligonucleotides at an appropriate density with single stranded polynucleotide molecules immobilised at intervals within the lawn of primers. The density of the templates may be the same density of clusters, namely $10^4$-$10^7$/mm$^2$, said density being capable of individual optical resolution of the individual molecules.

In a particular aspect, a method of the invention can be used to prepare clustered arrays of nucleic acid colonies, analogous to those described in WO 00/18957 or WO 98/44151 (the contents of which are herein incorporated by reference), by solid-phase amplification wherein the amplification efficiency of the templates of different sequence is normalised. The terms "cluster" and "colony" are used interchangeably herein to refer to a discrete site on a solid support comprised of a plurality of identical immobilised nucleic acid strands and/or a plurality of identical immobilised complementary nucleic acid strands. The term "clustered array" refers to an array comprising such clusters or colonies. In this context the term "array" can but does not necessarily require an ordered arrangement of clusters.

A further aspect of the invention provides a method of solid-phase nucleic acid amplification of a 5' and 3' modified library of template polynucleotide molecules which have common sequences at their 5' and 3' ends by carrying out a solid-phase nucleic acid amplification reaction under conditions wherein each of the template polynucleotide molecules in the library are amplified with equal, or approximately equal efficiency.

Approximately equal efficiency can be recognized as an intensity of AT rich clusters on an array, when viewed using an intercalator stain, that are less than twice the intensity of GC rich clusters on the array. The AT rich clusters can have less than twice as many template strands as the GC rich clusters. The ratio of the numbers of strands of each sequence may be such that the AT rich strands (defined as strands with greater than 80% AT composition) are less than 200% of the number of strands of AT poor sequence (defined as less than 20% AT composition). The level of % variation between AT rich and AT poor sequences may be 150%, 125%, 110%, 105% or 101%, each of which fails within the definition of approximately equal.

The term "common sequence," when used in reference to a collection of nucleic acid molecules, means a sequence that is the same for all of the nucleic acids in the collection. The nucleic acids in the collection can have a region of common sequence despite the presence of at least one other region in each of the nucleic acids that differs between the nucleic acids in the collection. As exemplified by the embodiments set forth above, all templates within a 5' and 3' modified library can contain regions of common sequence Y and Z at (or proximal to) their 5 and 3' ends, particularly wherein the common sequence at the 5' end of each individual template in the library is not identical and not fully complementary to the common sequence at the 3' end of said template. The term "library" refers to a collection or plurality of template molecules which can share common sequences at their 5' ends and common sequences at their 3' ends. Use of the term "5' and 3' modified library" to refer to a collection or plurality of template molecules should not be taken to imply that the templates making up the library are derived from a particular source. By way of example, a "5' and 3' modified library" can include individual templates within the library that have the same nucleotide sequence or that have different nucleotide sequences. Furthermore, the templates can, but need not be related in terms of sequence and/or source.

In various embodiments the invention can encompass use of so-called "mono-template" libraries, which comprise multiple copies of a single type of template molecule, each having common sequences at their 5 ends and their 3' ends, as well as "complex" libraries wherein many, if not all, of the individual template molecules comprise different target sequences (as defined below), although all share common sequences at their 5' ends and 3' ends. Such complex template libraries may be prepared from a complex mixture of target polynucleotides such as (but not limited to) random genomic DNA fragments, cDNA libraries etc. The invention may also be used to amplify "complex" libraries formed by mixing together several individual "mono-template" libraries, each of which has been prepared separately starting from a single type of target molecule (i.e., a mono-template). In particular embodiments more than 50%, or more than 60%, or more than 70%, or more than 80%, or more than 90%, or more than 95% of the individual polynucleotide templates in a complex library may comprise different target sequences, although all templates in a given library can share a common sequence at their 5' ends and a common sequence at their 3' ends.

Use of the term "template" indicates that one or both strands of a polynucleotide are capable of acting as templates for template dependent nucleic acid polymerisation catalysed by a polymerase. Such polynucleotides may not actually be used as templates in a subsequent enzyme-catalysed polymerisation reaction. Each strand of each template molecule in a library or other collection of nucleic acids may have the following structure, when viewed as a single strand:

5'-[known sequence I]-[target sequence]-[known sequence II]-3'

Wherein "known sequence I" is common to all template molecules in the library; "target sequence" represents a sequence which may be different in different individual template molecules within the library; and "known sequence II" represents a sequence also common to all template molecules in the library. Known sequences I and II can also include "primer binding sequence Y" and "primer binding sequence Z" and since they are common to all template strands in the library they may include "universal" primer-binding sequences, enabling all templates in the library to be ultimately amplified using universal primers comprising sequences Z' and Y, where Z' is complementary to Z. In particular embodiments, however, the common 5' and 3' end sequences denoted "known sequence I" and "known sequence II" need not be fully complementary to each other. For example, each individual template strand can contain different (and non-complementary) universal primer sequences at its 5' and 3' ends. It is generally advantageous for complex libraries of templates to be amplified by solid phase amplification to include regions of "different"

sequence at their 5' and 3' ends, which are nevertheless common to all template molecules in the library, especially if the amplification products are to be ultimately sequenced. For example, the presence of a common unique sequence at one end only of each template in the library can provide a binding site for a sequencing primer, enabling one strand of each template in the amplified form of the library to be sequenced in a single sequencing reaction using a single type of sequencing primer.

In a particular embodiment, the library is a library of single stranded polynucleotide molecules. Where the library comprises polynucleotide molecule duplexes, methods for preparing single stranded polynucleotide molecules from the library are known in the art. For example the library may be heated to a suitable temperature, or treated with hydroxide or formamide, to separate each strand of the duplexes before carrying out the method according to the invention. In another embodiment one strand of the duplex may have a modification, such as, for example biotin. Following strand separation by appropriate methods, the biotinylated strands can be separated from the complementary strands, using for example avidin coated micro-titre plates and the like, to effectively produce two single stranded populations or libraries. Thus a method according to the invention can be as applicable to one single stranded polynucleotide molecule as it is to a plurality of single stranded polynucleotide molecules.

In yet another embodiment, more than two, for example, three, four, or more than four different primer oligonucleotides may be grafted to one or more solid support. In this manner more than one library, with common sequences that differ between the libraries (wherein common sequences attached thereto are specific for each library), may be amplified, such as, for example libraries prepared from two different patients.

Use in Sequencing/Methods of Sequencing

In particular embodiments, the invention can also encompass methods of sequencing amplified nucleic acids generated by solid-phase amplification. Thus, the present disclosure provides a method of nucleic acid sequencing comprising amplifying a 5' and 3' modified library of nucleic acid templates as described above and carrying out a nucleic acid sequencing reaction to determine the sequence of the whole or a part of at least one amplified nucleic acid strand produced in the amplification reaction. In particular embodiments the amplification reaction is a solid-phase amplification reaction.

Sequencing can be carried out using any of a variety of suitable sequencing techniques, for example, a technique using nucleotides which are added successively to a free 3' hydroxyl group, resulting in synthesis of a polynucleotide chain in the 5' to 3' direction. The nature of the nucleotide added may be determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (referred to herein as "pyrosequencing"). Such pyrosequencing based techniques are particularly applicable to sequencing arrays of beads where the beads have been isothermally amplified and where a single template from the library molecule is amplified on each bead.

The initiation point for the sequencing reaction may be provided by annealing of a sequencing primer to a product of a solid-phase amplification reaction. In this connection, one or both of the adapters added during formation of a template 5' and 3' modified library may include a nucleotide sequence which permits annealing of a sequencing primer to amplified products derived by whole genome or solid-phase amplification of the template 5' and 3' modified library.

The products of particular solid-phase amplification reactions wherein both forward and reverse amplification primers are covalently immobilised on the solid surface are so-called "bridged" structures formed by annealing of pairs of immobilised polynucleotide strands and immobilised complementary strands, both strands being attached to the solid support at the 5' end. Arrays comprised of such bridged structures may provide inefficient templates for nucleic acid sequencing, since hybridisation of a conventional sequencing primer to one of the immobilised strands may not be favoured compared to annealing of this strand to its immobilised complementary strand under standard conditions for hybridisation.

In order to provide more suitable templates for nucleic acid sequencing, substantially all, or at least a portion of, one of the immobilised strands in the "bridged" structure may be removed in order to generate a template which is at least partially single-stranded. The portion of the template which is single-stranded will thus be available for hybridisation to a sequencing primer. The process of removing all or a portion of one immobilised strand in a "bridged" double-stranded nucleic acid structure may be referred to herein as "linearisation".

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker. Methods of linearization are detailed in co-pending application US 2009/0110128, whose contents are incorporated herein by reference in their entirety. It will be appreciated that a linearization step may not be essential if the solid-phase amplification reaction is performed with only one primer covalently immobilised and the other in free solution.

In order to generate a linearised template suitable for sequencing it is possible to remove the cleaved complementary strands in the bridged structure that remain hybridised to the uncleaved strand. This denaturing step can be included as a part of the 'linearisation process', and can be carried out by standard techniques such as heat or chemical treatment with hydroxide or formamide solution. In a particular embodiment, one strand of the bridged structure is substantially or completely removed by the process of chemical cleavage and denaturation. Denaturation can result in the production of a sequencing template that is partially or substantially single-stranded. A sequencing reaction may then be initiated by hybridisation of a sequencing primer to the single-stranded portion of the template.

Thus, particular embodiments of the invention can encompass methods wherein a nucleic acid sequencing reaction comprises hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s), or one or more of the bases present in the oligonucleotides, and thereby determining the sequence of a region of the template strand.

One particular sequencing method which can be used in accordance with the invention relies on the use of modified nucleotides having removable 3' blocks, for example as described in WO 04/018497, U.S. Pat. No. 7,057,026 and U.S. Pat. No. 6,664,079. Once the modified nucleotide has been incorporated into the growing polynucleotide chain complementary to the region of the template being sequenced there is no free 3'-OH group available to direct further sequence extension and therefore the polymerase cannot add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached thereto a different label, known to correspond to the particular base, to facilitate discrimination among the bases added at each incorporation step. Alternatively, a separate reaction may be carried out containing each of the modified nucleotides separately.

Modified nucleotides used in a sequencing method may carry a label to facilitate their detection. Particularly this is a fluorescent label. Each nucleotide type may carry a different fluorescent label. However the detectable label need not be a fluorescent label. Any label can be used which allows the detection of an incorporated nucleotide. One method for detecting fluorescently labelled nucleotides comprises using laser light of a wavelength specific for the labelled nucleotides, or the use of other suitable sources of illumination. The fluorescence from the label on the nucleotide may be detected by a CCD camera or by another suitable optical detector.

The invention is not intended to be limited to use of the sequencing method outlined above, as essentially any sequencing methodology which relies on successive incorporation or removal of nucleotides into or from a polynucleotide chain can be used. Suitable alternative techniques include, for example, Pyrosequencing, FISSEQ (fluorescent in situ sequencing), MPSS (massively parallel signature sequencing) and sequencing by ligation-based methods, for example as described in U.S. Pat. No. 6,306,597. Other methods of sequencing or detecting nucleic acids can be used as well.

A target polynucleotide to be sequenced using a method set forth herein may be any polynucleotide that it is desired to sequence. Using the amplification methods described herein it is possible to prepare a clustered array of template libraries starting from essentially any double or single-stranded target polynucleotide of known, unknown or partially known sequence. With the use of clustered arrays prepared by solid-phase amplification it is possible to sequence multiple targets of the same or different sequence in parallel. Sequencing may result in determination of the sequence of a whole or a part of the target molecule.

Clustered Arrays and their Use

Arrays generated using methods as described herein include amplified features on the array that all have a similar or substantially equal size or mass (or if detected can display substantially equal intensity) independent of their GC composition. Arrays prepared using previous amplification methods typically showed a wide variation in the intensity and size of features, with the AT rich amplicon populations becoming much brighter than the GC rich amplicon populations. The methods described herein give rise to an array of amplified nucleic acid clusters on a solid support wherein the clusters comprise GC and AT rich templates and the number of nucleic acid strands in each cluster is approximately equal. In some embodiments, the density of clusters on the array can be at least 200,000 per mm$^2$. Using methods of the invention, the lower limit of features on the array may be increased without losing representation of the GC rich sequences. For example the array may contain at least 300,000 clusters per mm$^2$. The array may contain at least 400,000, at least 500,000, at least 600,000, at least 700,000, at least 800,000, at least 900,000 or at least 1,000,000 clusters per mm$^2$.

Clustered arrays formed by the methods of the invention are suitable for use in applications usually carried out on ordered arrays such as micro-arrays. Such applications by way of non-limiting example include hybridisation analysis, gene expression analysis, genotyping analysis, protein binding analysis and the like. A clustered array may be sequenced before being used for downstream applications such as, for example, hybridisation with fluorescent RNA or binding studies using fluorescent labelled proteins.

Apparatus

Advantageously, solid phase amplification can be performed efficiently in a flow cell since it is a feature of the invention that the primers, template and amplified (extension) products all remain immobilised to the solid support and are not removed from the support at any stage during the amplification.

Such an apparatus may include one or more of the following:

a) at least one inlet b) means for immobilising primers on a surface (although this is not needed if immobilised primers are already provided);

c) means for substantially isothermal amplification of nucleic acids (e. g. denaturing solution, hybridising solution, extension solution, wash solution(s));

d) at least one outlet e) control means for co-ordinating the different steps required for the method of the present invention.

Other apparatuses are within the scope of the present invention.

A particularly useful apparatus can allow immobilised nucleic acids to be isothermally amplified. An apparatus may also include a source of reactants and detecting means for detecting a signal that may be generated once one or more reactants have been applied to the immobilised nucleic acid molecules. An apparatus may also be provided with a surface comprising immobilised nucleic acid molecules in the form of colonies, as described supra.

In a preferred embodiment as a volume of a particular suitable buffer in contact with a solid support is removed so it is replaced with a similar volume of either the same or a different buffer. Thus, buffers applied to a flow cell through an inlet can be removed via an outlet by a process of buffer exchange.

Desirably, a means for detecting a signal has sufficient resolution to enable it to distinguish between and among signals generated from different colonies. Instruments that are useful for detecting a fluorescent signal are described, for example, in WO 2007/123744, US 2010/0111768 and U.S. Pat. No. 7,329,860, the contents of which are incorporated by reference herein in their entireties.

Apparatuses of the present invention (of whatever nature) are preferably provided in automated form so that once they are activated, individual process steps can be repeated automatically.

EXAMPLES

Experimental Overview

Preparation of flowcells and other aspects of the Solexa/Illumina sequencing platform have been described in numerous patents and publications, for example Bentley et al; Accurate whole human genome sequencing using reversible terminator chemistry; Nature (2008) Nov. 6; 456(7218):53-9, US2009/0118128, US2010/0009871 and US2009/0088327, the contents of which are incorporated by reference in their entirety.

Flow cells grafted with two amplification primers were prepared according to standard Illumina procedures.

Template DNA Hybridisation

The DNA templates to be hybridised to the grafted flowcell were prepared using the standard Illumina sample preparation techniques (Illumina, Inc., San Diego, Calif.). Cluster creation was carried out using an Illumina Cluster Station. To obtain single stranded templates, the template library was first denatured in NaOH (to a final concentration of 0.1N) and subsequently diluted in cold (4° C.) hybridisation buffer (5×SSC 0.1% Tween 20) to working concentrations of 5 or 40 pM, depending on the desired cluster density/tile. After equilibrating the Illumina flowcell at 20° C., each lane was equilibrated by pumping hybridization buffer (60 µl/min, 120 µl). The temperature was then ramped up to 96° C. (1° C./sec) and 70 µl of denatured template was pumped inside each lane at 15 µl/min followed by a further 10 µl of denatured template pumped at 100 µl/min. The temperature was held at 96° C. for 5 minutes after which the flowcell was gradually cooled down to 40° C. (0.05° C./sec) to enable annealing to complementary adapter oligonucleotides immobilised on the flowcell surface. Unbound DNA molecules were removed with 75 µl of wash buffer (0.3× SSC, 0.1% Tween 20) pumped at 15 µl/min. The flowcell was then equilibrated in amplification premix (20 mM Tris pH 8.8, 10 mM (NH$_4$)$_2$SO$_4$, 2 mM MgSO$_4$, 0.1% Triton X-100, 2 M betaine) by pumping 70 µl of this solution at 15 µl/min. Finally, 95 µl of Taq mix (0.025 U/µl, 200 µM dNTP, in 1× amplification premix) were pumped inside the flowcell at (60 µl/min), after which the temperature was raised to 74° C. and held at 74° C. for 90 seconds to generate their surface-bound complements of the original template molecules. The original molecules were then removed by pumping them out of the flowcell after denaturing them in either formamide in the case of isothermal amplification or in Taq mix at high temperature in the case of thermal amplification. The remaining single stranded copy was the starting point for cluster creation.

Clusters were then prepared using different conditions according to the desired experiment:

Example 1a: Comparison of Equimolar and Skewed dNTP Concentrations

Two flow cells were seeded with monotemplates having a GC content ranging from 30 to 80%, (one monotemplate in each lane). The first flowcell was amplified using thermal amplification with standard dNTP concentrations (200 µM each nucleotide) for 30 cycles. The second flowcell was amplified using thermal amplification with standard dNTP concentrations (200 µM each nucleotide) for the first 5 cycles, then switched to 10 µM of dATP and dTTP and 390 µM of dCTP and dGTP for the following 25 cycles.

Figure 1:
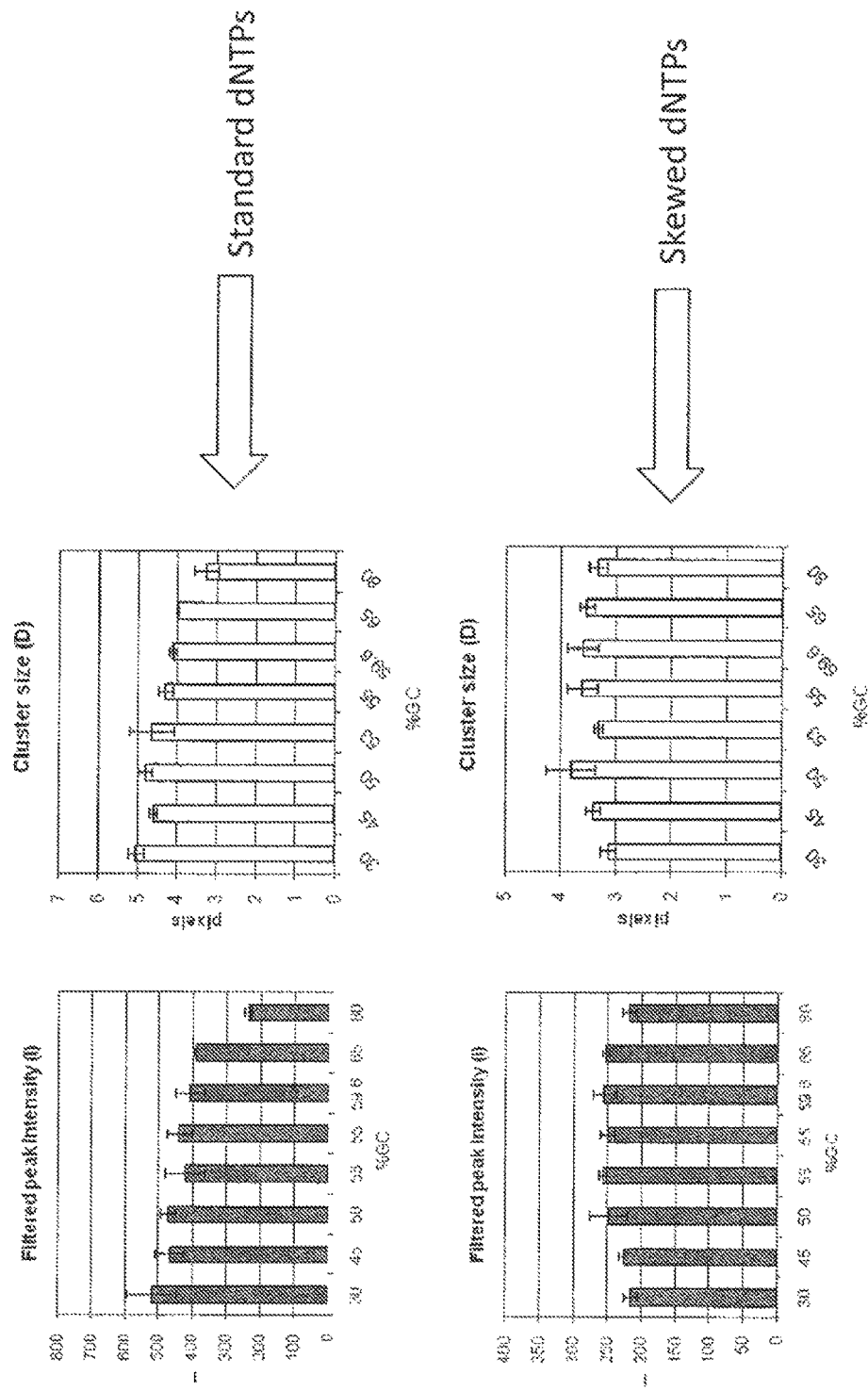
FIG. 1 shows exemplary data from an array of clusters grown with normal concentrations of nucleotides and skewed concentrations of nucleotides. Each of two 8 lane flowcells were seeded with different nucleic acid monotemplates in each lane. The GC content of the monotemplates ranged from between 30% to 80%. The first flowcell was amplified using thermocycling amplification with standard equimolar dNTP concentrations (200 µM each nucleotide) for 30 cycles. The second flowcell was amplified using thermocycling amplification with standard dNTP concentration (200 µM each nucleotide) for first 5 cycles, then switched to 10 µM of dATP and dTTP and 390 µM of dCTP and dGTP for the following 25 cycles. The amplified clusters were stained with the intercalating stain SyBr green and imaged.

The clusters were treated with the intercalator stain SyBr Green as described below and imaged. Representative data from each of the flow cells is shown in FIG. 1. The first flow cell shows that the AT rich (GC poor) monotemplates grow larger and showed more stained intensity than the GC rich clusters. In the second flowcell, the clusters in each of the 8 lanes are of similar brightness and intensity, showing that the amplification of the AT rich clusters has been inhibited by lowering the concentrations of the dATP and dTTP.

SYBR Green-I Staining

The chip was flushed with a 1/5000 dilution of SYBR Green-I in 100 mM sodium ascorbate in Tris-HCl buffer pH 8.0 for 2.5 min. at 60 µl/min/channel.

Visualisation

The clusters were visualised using an inverted epi-fluorescence microscope equipped with an EXFO Excite 120 illumination system and a CCD detector (ORCA ER from Hamamatsu). The filters used were the xf22 set from Omega Optical. The exposure power was normalised to 1 millijoule for each exposure.

Example 1b: Comparison of Increased Amplification Cycles on Normalised Cluster Intensity The template used was an *E. coli* library. Clusters were amplified under isothermal conditions at 60° C. for 5 cycles using successive cycles of formamide (28 µl, 30 µl/min), amplification premix mix (28 µl, 30 µl/min), amplification mix (36 µl at 30 µl/min 0.08 U/µl Bst polymerase+200 µM dNTPs in 1× amplification premix) and formamide (36 µl at 15 µl/min).

First, 5 cycles were carried out on all lanes using equimolar concentrations of nucleotides. Separate lanes in the flow cell were then treated differently as indicated below. Specifically, 21 additional cycles were carried out on all lanes using differing concentrations of nucleotides as described below. For 5 of the 8 lanes (lanes 3, 4, 5, 6, and 8), an additional 15 cycles of amplification with a lower concentration of dATP and dTTP was carried out. A comparison of two different polymerases (Bst and Pfu) was also carried out.

| Lane | CT2724 conc. | Conc. Of dCTP and dGTP | Conc. Of dATP and dTTP | Cycles of amp. | DNA Polymerase |
|---|---|---|---|---|---|
| 1 | 5 pM | 200 µM | 200 µM | 26 | Bst |
| 2 | 40 pM | 200 µM | 200 µM | 26 | Bst |
| 3 | 40 pM | 380 µM | 20 µM | 41 | Bst |
| 4 | 40 pM | 385 µM | 15 µM | 41 | Bst |
| 5 | 5 pM | 385 µM | 15 µM | 41 | Bst |
| 6 | 40 pM | 380 µM | 10 µM | 41 | Bst |
| 7 | 40 pM | 200 µM | 200 µM | 26 | Pfu |
| 8 | 40 pM | 395 µM | 5 µM | 41 | Pfu |

The flow cell was linearised, blocked and sequenced through 36 cycles of Illumina sequencing on an Illumina Genome Analyser using standard protocols.

Linearisation of surface-immobilised complementary oligo-A (oligo A: 5'-PS-TTTTTTTTTT-(diol)3-AATGA-TACGGCGACCACCGA-3' (SEQ ID NO:1)) was achieved by incubation with linearization mix (100 mM sodium periodate, 10 mM 3-aminopropan-1-ol, 20 mM Tris pH 8.0, 50% v/v formamide) for 20 minutes at 20° C. followed by a water wash. All exposed 3'-OH termini of DNA, either from the extended template or unextended surface oligonucleotides were blocked by dideoxy chain termination using a terminal transferase (0.25 U/µl, 2.4 µM ddNTP, 50 mM potassium acetate, 20 mM Tris acetate, 10 mM magnesium acetate, 1 mM dithiothreitol pH 7.9, 37° C., 30 minute incubation). Linearised and blocked clusters were denatured with 0.1N NaOH prior to hybridisation of the sequencing primer (0.5 µM in hybridisation buffer). Processed flowcells were transferred to the Illumina Genome Analyser for sequencing, which was carried out according to the Genome Analyser User Manual with standard protocols (Illumina, Inc., San Diego, Calif.).

Sequencing data from lanes 1, 2 and 6 can be seen in FIG. 2. FIG. 2 shows the effect of cluster density on the GC bias. At low template concentration (5 pM, lane 1) of fragmented E. coli DNA, there is little difference in sequence coverage between GC rich and GC poor regions of the genome as compared to higher concentrations of template DNA. At higher template concentrations (40 pM, lane 2), where the number of clusters on the surface is higher, the coverage of the GC rich regions of the genome starts to decrease. Lane 6 shows that amplification using varying dNTP concentrations (so called 'skewed' nucleotides) using the same 40 pM template concentration, recovers the GC bias to the same as the lower template concentration where GC bias was less apparent.

Example 2: Higher Concentrations of Betaine Reduce GC Bias

As shown in FIG. 3, concentrations of betaine above 2 M lower the size of clusters in a sequence dependent manner such that the AT rich clusters become proportionally smaller than the GC rich clusters, resulting in GC rich clusters and AT rich clusters of similar size. The lighter bars, corresponding to the AT rich templates, show a more substantial decrease than the darker bars, corresponding to the GC rich templates. FIG. 4 also shows higher concentrations of betaine result in less GC bias than lower concentrations of betaine. FIG. 5 is a normalised GC bias plot showing that betaine at 4M concentration gives less GC bias than betaine at 2 M concentration.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for amplifying nucleic acid templates of different sequences comprising:
   a) amplifying nucleic acid templates on a solid support in the presence of an additive capable of increasing efficiency of amplification of GC rich nucleic acid templates or decreasing efficiency of amplification of AT rich nucleic acid templates, wherein a subset of nucleotide types are incorporated into copies of the templates at a lower efficiency compared to at least one other type of nucleotide, thereby producing a plurality of different copies; and
   b) using the plurality of different copies as templates in a second cycle of amplification.

2. The method of claim 1, wherein the additive is betaine.

3. The method of claim 2, wherein the betaine is present at a concentration selected from the group consisting of 2.5, 3, 3.25, 3.5, 3.75, and 4 M.

4. The method of claim 2, wherein the betaine is present at a concentration between about 1 M and about 5 M.

5. The method of claim 1, wherein the method comprises at least one cycle of amplification using four nucleotide types which are not present at the same concentration.

6. The method of claim 5, wherein the amplification process also comprises at least one cycle using four nucleotide types which are present at the same concentration.

7. The method of claim 6, wherein the cycle using four nucleotide types which are present at the same concentration is followed by at least one cycle of amplification using four nucleotide types which are not present at the same concentration.

8. The method of claim 1, wherein the nucleotides are deoxynucleotide triphosphates selected from the group consisting of dATP, dTTP, dCTP, and dGTP.

9. The method of claim 8, wherein the concentration of dATP or dTTP is less than the concentrations of dGTP and dCTP.

10. The method of claim 9, wherein the concentration of dATP or dTTP is less than half, less than one quarter, or less than one tenth the concentration of dGTP and less than half the concentration of dCTP.

11. The method of claim 8, wherein the concentration of dATP or dTTP is less than 20 µM or less than 10 µM.

12. The method of claim 1, comprising the use of a T or A nucleotide analogue which makes the AT base pair interaction stronger.

13. The method of claim 1, comprising the use of a T or A nucleotide analogue which is incorporated by a polymerase with lower efficiency than dATP or dTTP.

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: Oligo A

<400> SEQUENCE: 1
tttttttttt aatgatacgg cgaccaccga                    30

14. The method of claim 13, wherein the T nucleotide analogue is 2-thio dTTP.

15. The method of claim 1, comprising the use of a T or A nucleotide analogue which causes a strand termination upon incorporation.

16. The method of claim 15, wherein the strand termination is reversible.

17. The method of claim 15, comprising the use of dUTP as a partial replacement for dTTP.

18. The method of claim 17, comprising the use of an archaeal polymerase.

19. The method of claim 18, wherein the archaeal polymerase is Pfu polymerase or a derivative thereof.

* * * * *